US008777839B2

(12) United States Patent
Kondoh et al.

(10) Patent No.: US 8,777,839 B2
(45) Date of Patent: Jul. 15, 2014

(54) SHOCK ABSORBING MECHANISM AND MEDICAL INSTRUMENT

(75) Inventors: Nobuko Kondoh, Tokyo (JP); Tatsutoshi Hashimoto, Tokyo (JP)

(73) Assignee: Olympus Medical Systems Corp. (JP)

( * ) Notice: Subject to any disclaimer, the term of this patent is extended or adjusted under 35 U.S.C. 154(b) by 1108 days.

(21) Appl. No.: 12/702,421

(22) Filed: Feb. 9, 2010

(65) Prior Publication Data

US 2010/0217072 A1    Aug. 26, 2010

Related U.S. Application Data

(63) Continuation-in-part of application No. 12/551,618, filed on Sep. 1, 2009, now Pat. No. 8,460,276.

(60) Provisional application No. 61/093,492, filed on Sep. 2, 2008.

(51) Int. Cl.
  *A61B 1/00*    (2006.01)
  *A61B 17/00*    (2006.01)

(52) U.S. Cl.
  USPC ............... 600/101; 600/146; 600/149; 606/1

(58) Field of Classification Search
  USPC ............... 600/101, 141, 146, 149, 150, 139; 606/1
  See application file for complete search history.

(56) References Cited

U.S. PATENT DOCUMENTS

| | | | | |
|---|---|---|---|---|
| 4,718,407 A | * | 1/1988 | Chikama | 600/150 |
| 5,472,017 A | | 12/1995 | Kovalcheck | |
| 5,683,412 A | * | 11/1997 | Scarfone | 606/205 |
| 2002/0143238 A1 | * | 10/2002 | Hino et al. | 600/146 |
| 2005/0065397 A1 | | 3/2005 | Saadat et al. | 600/104 |
| 2007/0225641 A1 | | 9/2007 | Schneider et al. | |
| 2007/0299387 A1 | | 12/2007 | Williams et al. | |
| 2008/0139886 A1 | * | 6/2008 | Tatsuyama | 600/146 |
| 2008/0139887 A1 | * | 6/2008 | Fitzpatrick | 600/153 |

FOREIGN PATENT DOCUMENTS

| | | |
|---|---|---|
| JP | B-39-029401 | 12/1964 |
| JP | U-57-069019 | 4/1982 |
| JP | A-04-078782 | 3/1992 |
| JP | A-2000-037390 | 2/2000 |
| JP | A-2005-204728 | 8/2005 |
| JP | A-2005-261521 | 9/2005 |
| JP | A-2006-516910 | 7/2006 |

(Continued)

OTHER PUBLICATIONS

Extended European Search Report dated Feb. 3, 2010 in corresponding European Patent Application No. 09011208 (English language).

(Continued)

*Primary Examiner* — Ahmed Farah
(74) *Attorney, Agent, or Firm* — Ostrolenk Faber LLP

(57) ABSTRACT

A shock-absorbing mechanism includes a shaft having a linear member wound therearound, a base having a relative position fixed to a first end of the linear member and formed with a shock-absorbing space which spreads toward the radial outside from the outer peripheral surface of the shaft, and a passage formed in the base in communication with the shock-absorbing space and the outside of the base and causing a second end of the linear member to extend to the outside of the base.

6 Claims, 36 Drawing Sheets

(56) References Cited

FOREIGN PATENT DOCUMENTS

| JP | 2006-331123 | * | 12/2006 |
| JP | 2007-030145 | | 2/2007 |
| JP | 2007-097620 | | 4/2007 |
| WO | WO 2004/064600 | | 8/2004 |
| WO | WO 2007/002713 | | 1/2007 |

OTHER PUBLICATIONS

Office Action issued by USPTO on Jul. 12, 2012 in connection with corresponding U.S. Appl. No. 12/551,618.
Office Action mailed by Japanese Patent Office on May 14, 2013 in connection with corresponding Japanese Patent Application No. JP 2009-201790 with English translation.

* cited by examiner

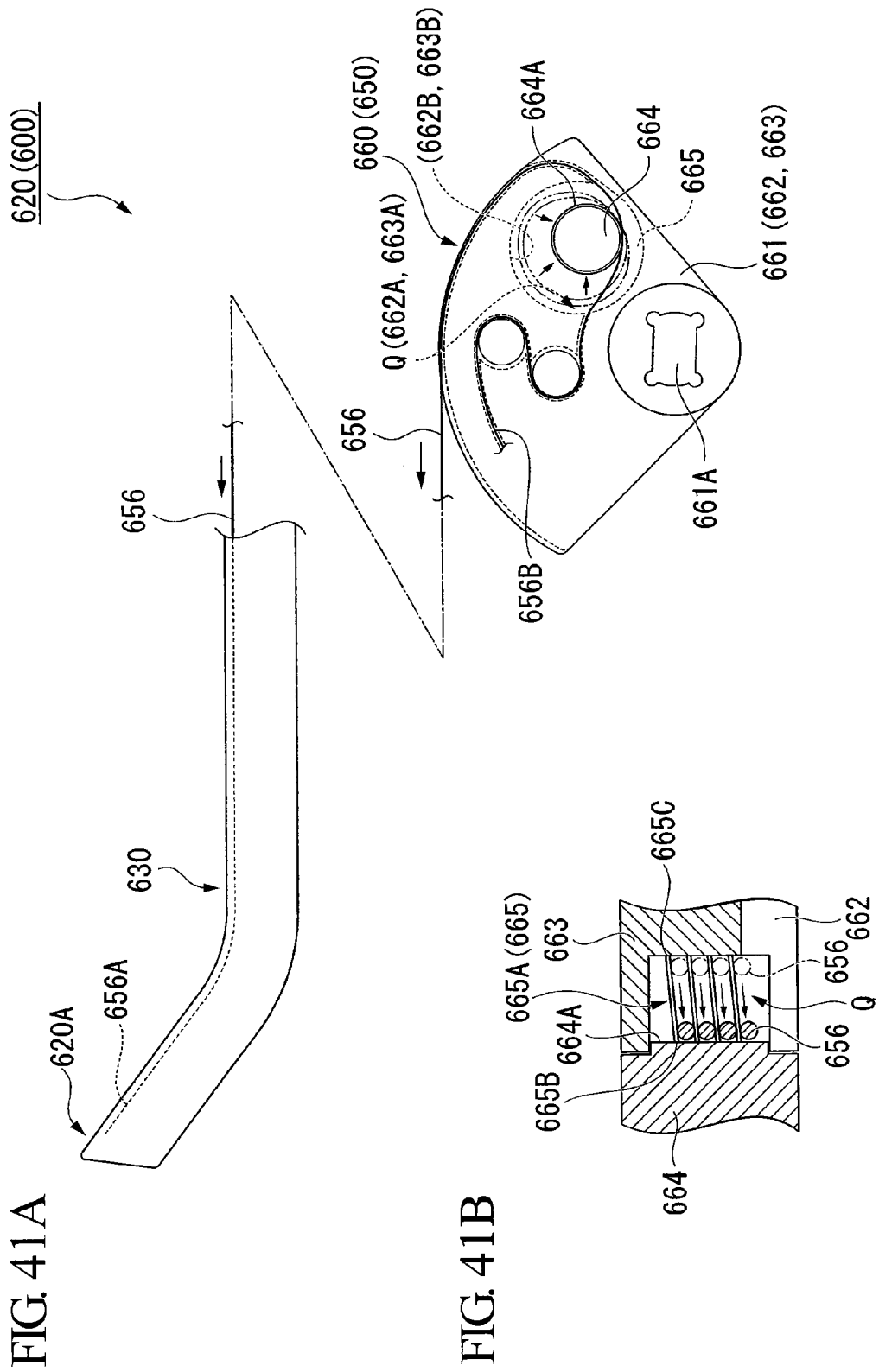

SHOCK ABSORBING MECHANISM AND MEDICAL INSTRUMENT

CROSS REFERENCE TO RELATED APPLICATIONS

The present application is a partial continuation application of U.S. application Ser. No. 12/551,618 "MANIPULATION MECHANISM AND MEDICAL INSTRUMENT" filed on Sep. 1, 2009, the entire contents of which are incorporated herein by reference.

BACKGROUND OF THE INVENTION

1. Field of the Invention

The present invention relates to a shock-absorbing mechanism and medical instrument, and, more particularly to a medical instrument which is used while being inserted into a body cavity in combination with, for example, a soft endoscope, and a shock-absorbing mechanism attached to the medical instrument.

2. Background Art

As a method of performing a medical action such as an observation or a treatment on the internal organs of a human body, there is known a laparoscopic surgery which performs a surgical technique by forming a plurality of openings in an abdominal wall instead of making a large incision in an abdominal wall, and inserting treatment instruments such as an abdominoscope or clamp into the respective openings. In such a surgery, since only small openings are formed in the abdominal wall, it is advantageous in that stress on the patient is reduced.

In addition, as a method of reducing the stress to the patient, a method has been proposed for performing a surgical technique by inserting a soft endo scope through a natural opening such as patient's mouth, nose, or anus. An example of an endoscope device (medical instrument) used in such a surgical technique is disclosed in US Patent Application Laid-open No. 2005/0065397.

In the disclosed endoscope device, arm portions of which distal ends can be bent are respectively inserted through a plurality of lumens disposed in a soft inserting portion inserted through a patient's mouth. When treatment tools are respectively inserted through the arm portions, the treatment tools can be made to approach a treatment portion in different directions, and to continuously perform a plurality of surgical techniques in a state in which one endoscope is inserted into a body cavity.

In addition, in the arm portion (manipulation mechanism) disclosed in the above-described specification, four pulling wires are disposed along the arm portion so as to be located at the same interval in the circumferential direction. In the pulling wires, the proximal ends are attached to a steering opening (oscillating body) in the base end of the arm portion, and the distal ends are attached to the distal end of the arm portion. In addition, it is possible to change the direction of the treatment portion protruding from the distal end of the arm portion by curving the distal end of the arm portion in such a manner that the proximal end of the treatment tool communicating with the opening and the arm portion is inclined so as to rotate the opening with respect to the arm portion.

SUMMARY OF THE INVENTION

A first aspect of the present invention is a shock-absorbing mechanism including a shaft having a linear member wound therearound; a base having a relative position fixed to one end of the linear member and being formed with a shock-absorbing space which spreads toward the radial outside from the outer peripheral surface of the shaft; and a passage formed in the base in communication with the shock-absorbing space and the outside of the base and causing the other end of the linear member to extend to the outside of the base.

A second aspect of the present invention is a medical instrument including a shock-absorbing mechanism having a shaft having a linear member wound therearound; a base having a relative position fixed to one end of the linear member, being formed with a shock-absorbing space which spreads toward the radial outside from the outer peripheral surface of the shaft, and oscillating around an oscillating shaft parallel to an center axis of the shaft, thereby pulling the other end of the linear member; a passage formed in the base in communication with the shock-absorbing space and the outside of the base and causing the other end of the linear member to extend to the outside of the base; a tubular bending operating portion having the other end of the linear member fixed thereto, and performing a bending operation as the other end of the linear member is pulled in the axial direction of the linear member; an inserting portion having a proximal end of the bending operating portion fixed to the distal end thereof, and having the linear member arranged therein; and a manipulation portion having a handle portion which turns the base around the oscillating shaft, and being fixed to the inserting portion.

BRIEF DESCRIPTION OF THE DRAWINGS

FIG. 41A is an operation explanatory view for explaining the operation of the overtube of the modified example when used, and FIG. 41B is an explanatory view showing the function of the partition wall member.

DETAILED DESCRIPTION OF THE INVENTION

Respective embodiments of the present invention will be described below. In addition, the basic structure of an endoscope device of the present invention is disclosed in U.S. application Ser. No. 12/551,618 and U.S. application Ser. No. 11/652,880, which are relevant to the present application, and the disclosed contents thereof are incorporated into the following description by reference.

First Embodiment

An endoscope device 1 of the present embodiment is provided to perform a treatment in a relatively narrow space, such as the inside of a digestive tract, and enables single operator to perform endoscope manipulation and treatment manipulation. In addition, a portion of the apparatus is omitted in some drawings for convenience of description.

Figure 1:
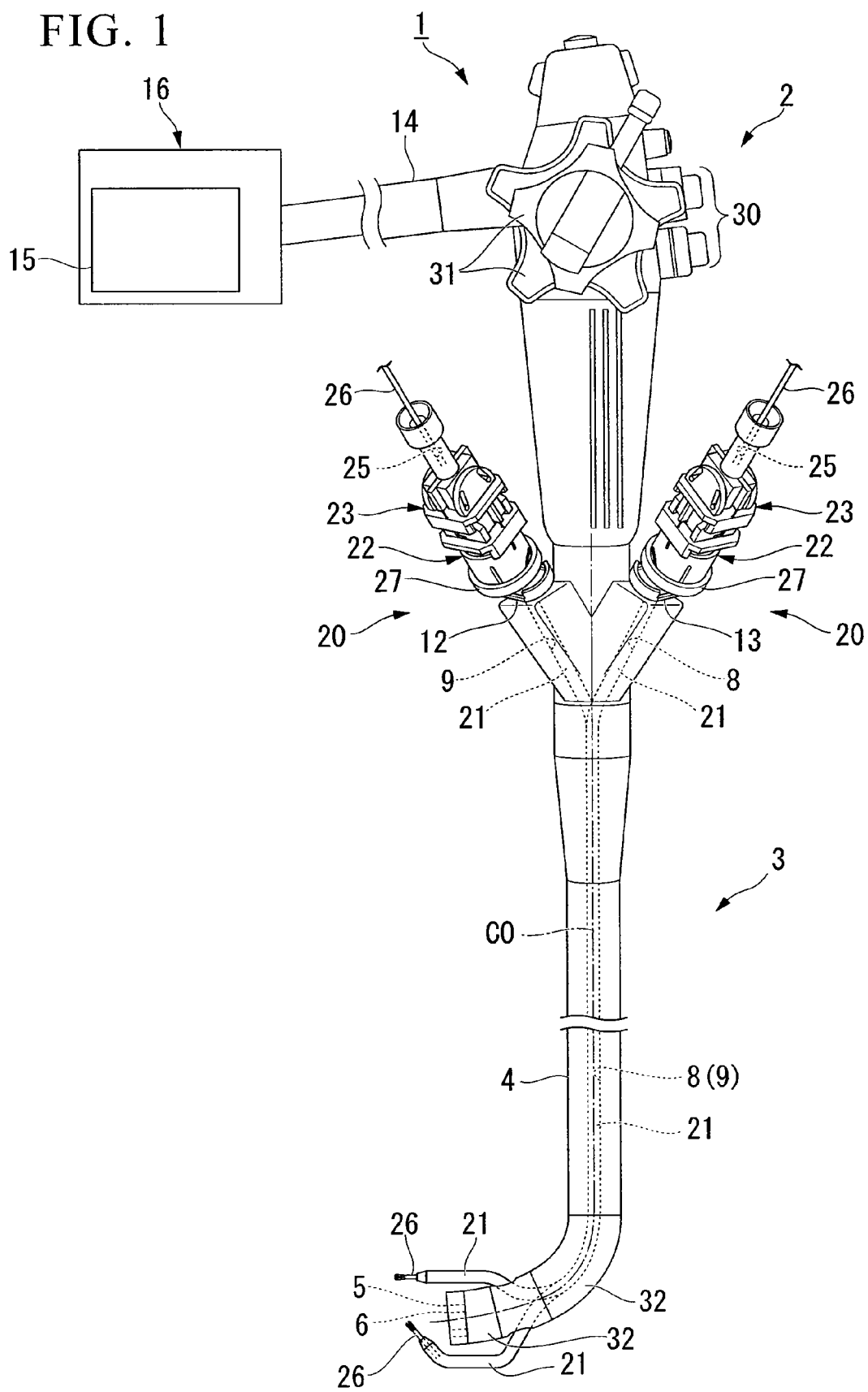
FIG. 1 is an overall view showing an endoscope device in a first embodiment of the present invention.

As shown in FIG. 1, in the endoscope device 1, a tubular endoscope inserting portion 3 is adapted so as to extend integrally from one end of an endoscope manipulation portion 2, and two arm mechanisms (medical instrument) 20 are assembled.

The endoscope inserting portion 3 is long and flexible, and the configuration thereof is the same as that described in U.S. application Ser. No. 11/652,880. That is, the endoscope inserting portion 3 includes a sheath 4 which covers an outer peripheral surface and has flexibility, an illumination mechanism 5 which radiates illumination light to the front, and an observation mechanism 6 which observes the front, and has an imaging device, such as a CCD (not shown). The inside of the endoscope inserting portion 3 is formed with a first lumen (work channel) 8 and a second lumen (work channel) 9 which continue from the distal end to the endoscope manipulation portion 2.

The endoscope manipulation portion 2 is provided with forceps inlets 12 and 13 which communicate with the first lumen 8 and the second lumen 9, respectively, and a control mechanism 16 having a monitor 15 which is connected via a universal cable 14. The control mechanism 16 has a light source (not shown), and supplies illumination light to the illumination mechanism 5. An image observed by the observation mechanism 6 is sent to the control mechanism 16 through the universal cable 14, is subjected to proper image processing, and is displayed on the monitor 15.

In addition to these, the endoscope manipulation portion 2 is provided with switches 30 and angle knobs 31. The switches 30 are operated, for example, when air supply, water supply, or suction is performed through the first lumen 8. The angle knobs 31 is used when a third bending portion 32 (which will be described later) of the endoscope inserting portion 3 is bent in four directions with respect to the axis.

Figure 2:
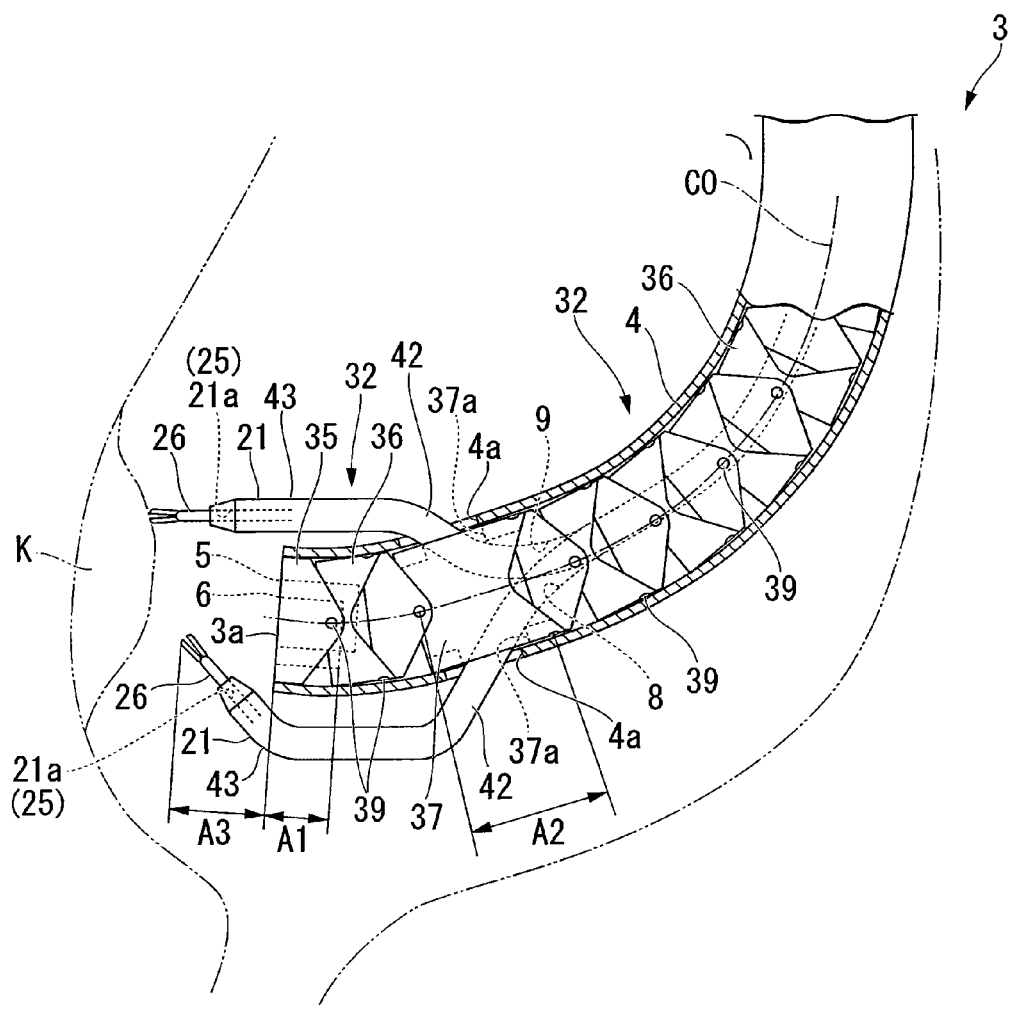
FIG. 2 is an enlarged view when a portion of the distal end of an inserting portion of the endoscope device is broken away.

As shown in FIG. 2, similarly to a well-known configuration, a plurality of substantially tubular bending pieces 36 is connected together and arranged over a certain range in the direction of a center axis C0 of the endoscope inserting portion 3 inside the endoscope inserting portion 3 so that the third bending portion 32 of the distal end of the endoscope inserting portion 3 can be bent with respect to the center axis C0.

A topped tubular first supporting piece 35 which has the illumination mechanism 5 and the observation mechanism 6 attached to the front end surface thereof, a plurality of bending pieces 36, a substantially tubular second supporting piece 37 in which a pair of openings 37a is formed at facing positions of side surfaces, and a plurality of bending pieces 36 are arranged in this order from the distal end inside the endoscope inserting portion 3. The first supporting piece 35 and the bending piece 36, the second supporting piece 37 and the bending piece 36, and the bending pieces 36 are rotatably connected together by a plurality of hinges 39, respectively, which is arranged so as to be orthogonal to the center axis C0 of the endoscope inserting portion 3 and be alternate as seen from the direction of the center axis C0.

Distal ends of four endoscope manipulating wires (not shown) are attached to the inner surface of the proximal end of the first supporting piece 35 at regular intervals along the circumferential direction, and endoscope manipulating wires which are arranged at facing positions constitutes a pair. Proximal ends of the two pairs of endoscope manipulating wires are inserted through the inside of the endoscope inserting portion 3 and the endoscope manipulation portion 2, and are fixed to the aforementioned angle knobs 31, respectively. The third bending portion 32 can be bent in four directions with respect to the center axis C0 by rotating the angle knobs 31.

At the distal end of the endoscope inserting portion 3, the first lumen 8, and the second lumen 9 are formed so as to communicate with the openings 37a of the second supporting piece 37, respectively, while being separated from the center axis C0 of the endoscope inserting portion 3.

In the present embodiment, at the distal end of the endoscope inserting portion 3, the ranges of the lengths A1 of the first supporting piece 35 and the ranges of the length A2 of the second supporting piece 37 along the center axis C0 are a hard range where the endoscope inserting portion 3 cannot be bent, and the other range becomes a soft range where the endoscope inserting portion 3 can be bent.

As shown in FIG. 1, each arm mechanism 20 has a long tubular arm portion 21 (inserting portion) which can be bent, a shaft-shaped main body 22 which is connected to the arm portion 21, and an arm manipulation portion (manipulation mechanism) 23 which is attached to the main body 22 so as to operate the bending of the front end of the arm portion 21. A treatment tool 26, such as grip forceps, can be inserted through a channel 25 which is formed so that the arm portion 21, the main body 22, and the arm manipulation portion 23 communicate with each other so as to be able to advance or retreat. In the present embodiment, two arm mechanisms 20 through which the treatment tools 26 are inserted are used, the arm portions 21 are detachably inserted through the first lumen 8 and the second lumen 9 so as to advance or retreat therein, and the main bodies 22 are attached to the forceps inlets 12 and 13, respectively. In addition, each arm portion 21 is rotatable around its own axe within the first lumen 8 and the second lumen 9.

The arm mechanisms 20 inserted through the lumens 8 and 9 are attached to the forceps inlets 12 and 13, respectively, so that the movements of the arm manipulation portions 23 do not interfere with each other, and proximal ends of the arm mechanism are separated from each other at a certain angle to the center axis C0 of the endoscope inserting portion 3.

In addition, in the present embodiment, grip forceps have been used as the treatment tools 26. However, the present invention is not limited thereto, and high-frequency knives, snares, etc. can be used as the treatment tools 26.

Inside each arm portion 21, almost similarly to the endoscope inserting portion 3 mentioned above, bending pieces (not shown) are connected together and arranged over a certain range in the direction of the center axis of the arm portion 21 at the distal end of the arm portion.

Distal ends of four arm portion manipulating wires (first operating members and second operating members) (not shown) are attached to the inner surfaces of the proximal end of the bending pieces arranged on the most distal end of the arm portions 21 at regular intervals along the circumferential direction, and arm portion manipulating wires which are arranged at facing positions constitutes a pair. The two pairs of arm portion manipulating wires are inserted through arm portion operating sheaths (not shown) which are fixed within the arm portions 21, and proximal ends of the arm portion manipulating wires extend to the arm manipulation portions 23 of the arm mechanisms 20, respectively. A first bending portion (bending portion) 43 can be bent by pulling arm portion manipulating wires.

In addition, as shown in FIG. 2, in the arm portions 21, distal ends of a pair of second bending manipulating wires (not shown) is attached to the inner surfaces of the bending pieces arranged at second bending portions 42 which hit intermediate portions of the bending pieces connected over a certain range. The second bending manipulating wires are inserted through second bending manipulation sheaths (not shown) which are arranged and fixed within the arm portions 21, and proximal ends of the second bending manipulating wires extend to the main bodies 22 of the arm mechanisms 20, respectively.

The arm portions 21 are inserted through the lumens 8 and 9 and the openings 4a formed in the sheaths 4, respectively, and protrudes to the front of a distal end surface 3a of the endoscope inserting portion 3.

Figure 3:
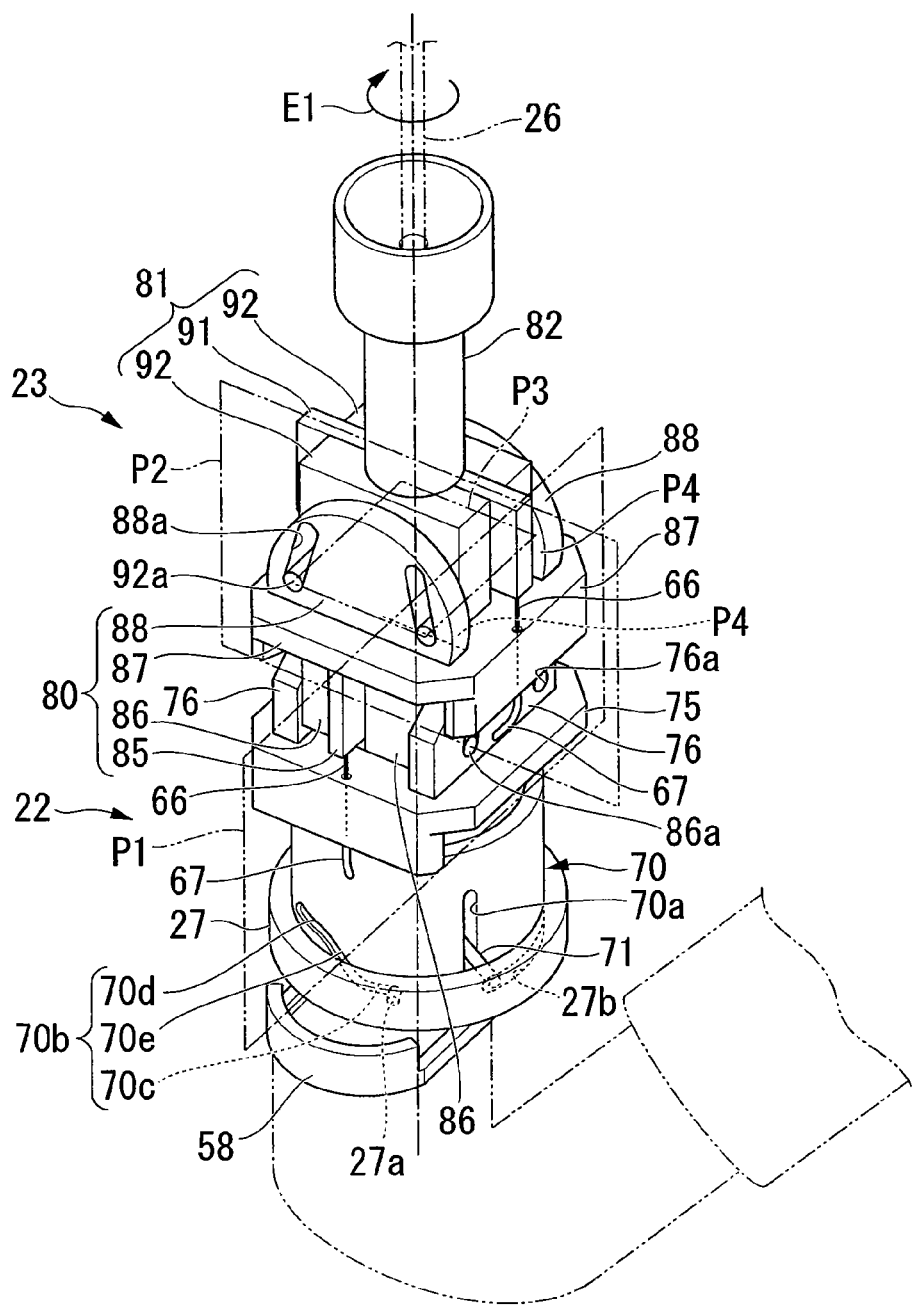
FIG. 3 is a perspective view of main section of an arm mechanism of the endoscope device.
Figure 4:
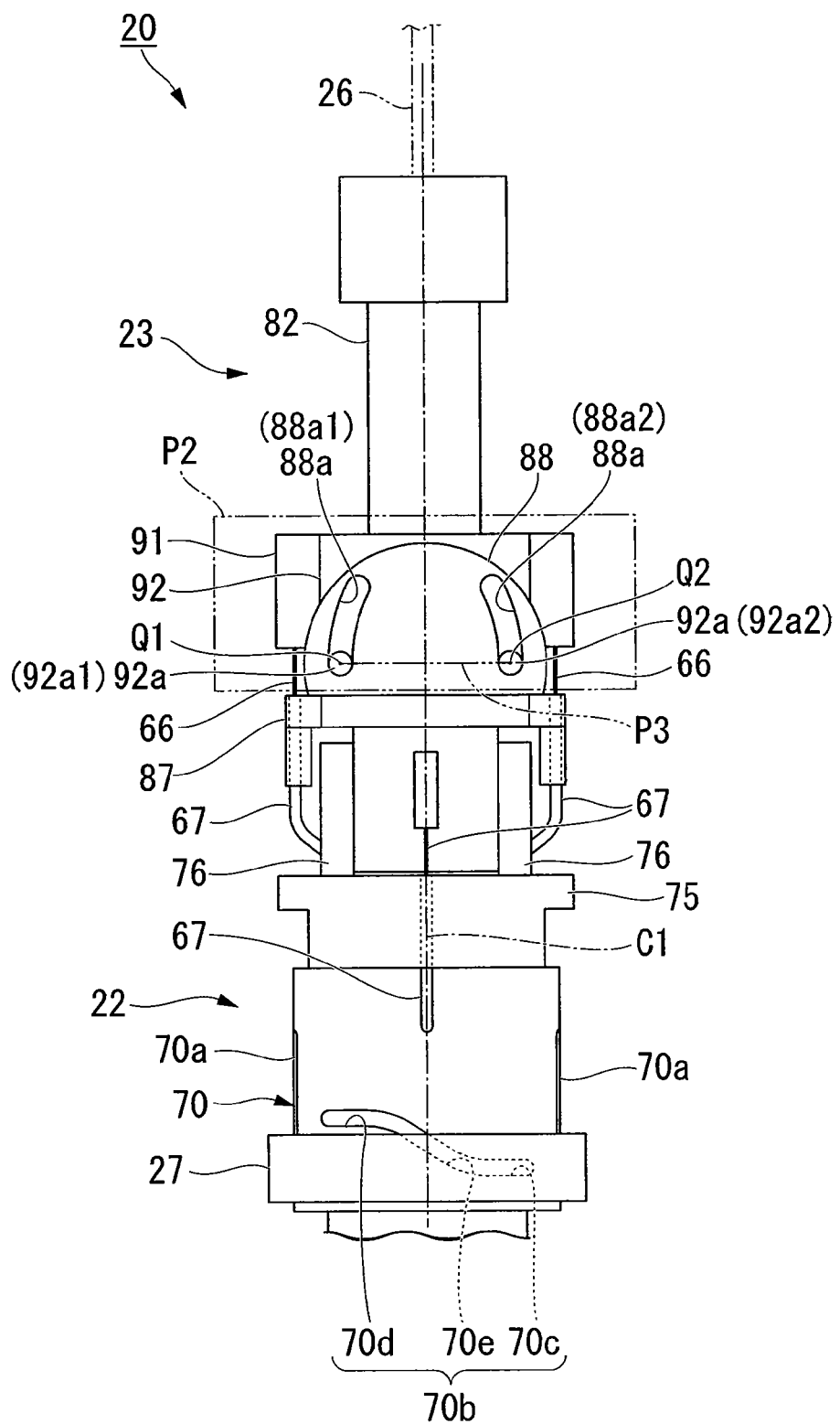
FIG. 4 is a plan view of the main section of the arm mechanism.
Figure 5:
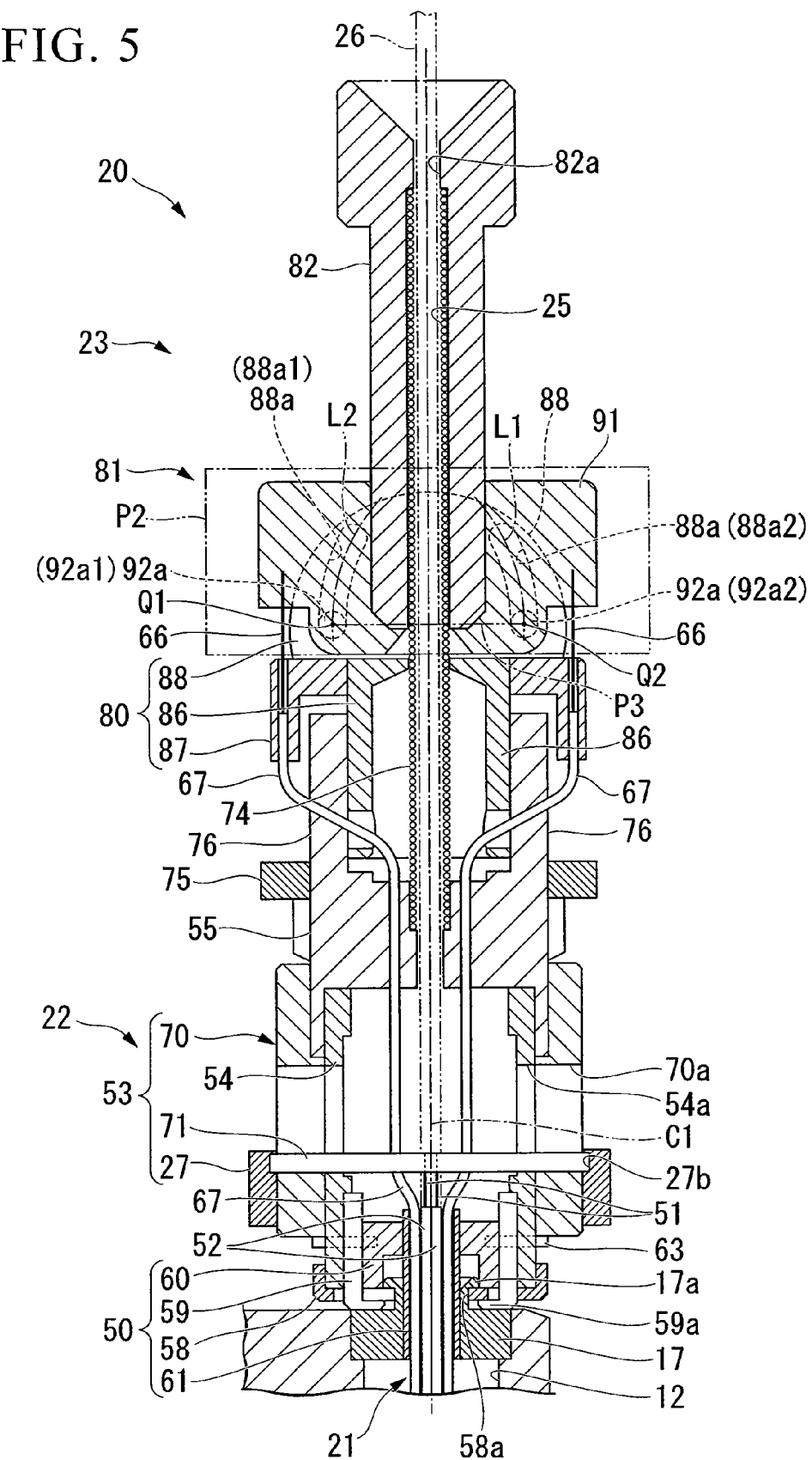
FIG. 5 is a sectional view of the main section of the arm mechanism.

Next, the configuration of the main body 22 and arm manipulation portion 23 of each arm mechanism 20 will be described in detail with reference to FIGS. 3 to 5. In addition, FIGS. 3 to 5 show a state in which a second bending manipulating ring 27 which will be described later has been pushed in and lowered, for the convenience of description. In addition, since the forceps inlet 12 and the forceps inlet 13 have the same configurations, description will be made using the forceps inlet 12 as an example.

The main body 22 includes an engagement mechanism 50 which engages with a cap 17 of the forceps inlet 12, a second bending manipulation mechanism 53 which pulls a proximal end of a second bending manipulating wire 51, a substantially cylindrical first main body member 54 to which the engagement mechanism 50 and the second bending manipulation mechanism 53 are attached, and a substantially cylindrical second main body member 55 which is coaxially fixed to the proximal end of the first main body member 54, and supports the arm manipulation portion 23 in an oscillating manner.

The engagement mechanism 50 includes a sliding member 58 which is formed in the shape of a plate, and engages with the cap 17, a guide ring 59 which supports the sliding member 58, a substantially cylindrical supporting member 60 which support the sliding member 58 between the supporting member and the guide ring 59, and a tubular connecting pipe 61 which is arranged on an axis C1 of the main body 22, is fixed to the supporting member 60 and is connected to the arm portion 21.

Since a substantially circular hole 58a is formed at a central portion of the sliding member 58, the sliding member 58 moves in a direction orthogonal to the axis C1 of the main body 22, whereby the hole 58a engages with a circular flange portion 17a formed in the cap 17, and the engagement mechanism 50 of the main body 22 is fixed to the forceps inlet 12. The guide ring 59 is formed from, for example, metal, such as stainless steel, and is composed of a tubular main body, and a ring-shaped claw portion 59a which protrudes radially inward from one end of the main body and sandwiches the sliding member 58 along with the flange portions 17a.

Moreover, the first main body member 54, the guide ring 59, and the supporting member 60 are fixed by a pin member 63 from the side surface of the first main body member 54. In addition, the second bending manipulation sheath 52 and the arm portion operating sheaths 67 are fixed to the connecting pipe 61.

As such, since the guide ring 59 is formed from metal, such as stainless steel, even if a large torque acts on the arm mechanism 20 with the hole 58a of the sliding member 58 as a center when the arm manipulation portion 23 is oscillated, the claw portion 59a of the guide ring 59 to which a particularly large torque is applied can be prevented from being damaged.

The second bending manipulation mechanism 53 includes a tubular guide member 70 which is fixed to the radial outside of the first main body member 54, a ring-shaped second bending manipulating ring 27 which is arranged on the radial outside of the guide member 70, and a rod member 71 which is locked to the second bending manipulating ring 27, and to which a proximal end of the second bending manipulating wire 51 adapted to be movable along the axis C1 is attached.

A pair of facing slits 70a and slit 54a which is formed along the axis C1, and communicate with each other is formed in the side surfaces of the guide member 70 and the first main body member 54, respectively.

Two grooves 70b are formed at facing positions on the outer peripheral surface of the guide member 70. More specifically, each groove 70b is formed substantially spirally as a whole such that a first groove 70c and a second groove 70d formed on the surfaces orthogonal to the axis C1, and a third groove 70e which is formed spirally so as to move to the proximal end as rotating in a direction E1 about the axis C1 are connected in order of the first groove 70c, the third groove 70e, and the second groove 70d.

Especially, as shown in FIG. 3, a pair of facing convex portions 27a which protrude radially inward is formed on the inner peripheral surface of the second bending manipulating ring 27, and engages with the grooves 70b of the guide member 70, respectively. In addition, a pair of grooves 27b is formed in the circumferential direction at facing positions on the inner peripheral surface of the second bending manipulating ring 27. The rod member 71 is inserted through the slit 70a of the guide member 70, and the slit 54a of the first main body member 54, and is locked to the grooves 27b of the second bending manipulating ring 27 at both ends of the rod member 71.

Since the second bending manipulation mechanism 53 is configured in this way, when the second bending manipulating ring 27 arranged at the position shown in FIGS. 3 to 5 is rotated in the direction E1 about the axis C1, the second bending manipulating ring 27 moves to the proximal end while rotating in a direction E1 as the convex portions 27a moves to the proximal end of the main body 22 along the grooves 70b. Since the rod member 71 is locked to the grooves 27b of the second bending manipulating ring 27, and is inserted through the slit 70a and the slit 54a, both ends of the rod member 71 move in the circumferential direction of the second bending manipulating ring 27 inside the grooves 27b, and the rod member 71 moves to the proximal end along to the slit 70a without rotating in the direction E1. In this way, the rod member 71 can pull the proximal end of the second bending manipulating wire 51 without twisting the second bending manipulating wire 51. Then, when the convex portion 27a reaches the second groove 70d of the groove 70b, the second bending manipulating ring 27 is fixed to the guide member 70 by the friction between the convex portion 27a and the second groove 70d, and even if an operator releases his/her hand from the second bending manipulating ring 27, a state in which the second bending manipulating wire 51 has been pulled is maintained.

As shown in FIGS. 3 to 5, the second main body member 55 is provided with a spring member 74 which is arranged inside the second main body member 55, extends to the proximal end along the axis C1, and has one end fixed thereto; a substantially flat plate-like first sheath attachment member 75 which is arranged on the outer peripheral surface of the proximal end of the second main body member 55, and has a pair of arm portion operating sheaths 67 attached thereto; and a pair of plate-like first guide members (supporting bodies) 76 which are arranged on the surface of the second main body member 55 at the proximal end, and is formed with a pair of slits (a first groove and a second groove) 76a to engage with a first oscillating portion 80 which will be described hereinafter. In addition, the shape of the slits 76a will be described in detail later.

In addition, the arm manipulation portion 23 includes a first oscillating portion 80 which is connected to the first guide members 76 and oscillates on a plane (first imaginary plane) P1 including the axis C1, a second oscillating portion 81 which is connected to the first oscillating portion 80 and oscillates on a plane (second imaginary plane) P2 orthogonal to the plane P1 including the axis C1, and a cylindrical manipulation stick (oscillating body) 82 which is fixed to the second oscillating portion 81. The first oscillating portion 80, the second oscillating portion 81 and the manipulation stick 82 are arranged so as to line up in this order on the axis C1 of the main body 22.

The first oscillating portion 80 includes a plate-like first wire attachment plate 85 to both ends of which proximal ends of arm portion manipulating wires 66 are attached; a pair of first supporting members 86 which are fixed so as to sandwich the first wire attachment plate 85, and are provided with a pair of columnar shaft members (a first convex portion and a second convex portion) 86a which engage with the slits 76a of the first guide members 76; a substantially flat plate-like second sheath attachment member 87 which is arranged on the outer peripheral surfaces of the proximal ends of the pair of first supporting members 86, and has a pair of arm portion operating sheaths 67 attached thereto; and a pair of plate-like second guide members (supporting bodies) 88 which are arranged on the surfaces of the pair of first supporting members 86 at the proximal end, and is formed with a pair of slits (a first groove and a second groove) 88a to engage with a second oscillating portion 81 which will be described. The first wire attachment plate 85 and the pair of first supporting members 86 constitute an oscillating body.

The first wire attachment plate 85, the pair of first supporting members 86, and the pair of first guide members 76 are formed, respectively so as to become symmetrical to the plane P1. Each arm portion manipulating wire 66 extends to the distal end (the other side) of the arm portion 21 through one of the shaft members 86a.

The pair of shaft members 86a are formed so as to be separated from each other and protrude from the first supporting members 86. As the pair of shaft members 86a engages with the slits 76a of the pair of first guide members 76, respectively, and the slits 76a guide the shaft members 86a, the first supporting members 86 are regulated so as to oscillate along the plane P1.

In addition, the second oscillating portion 81 includes a plate-like second wire attachment plate 91 to both ends of which the proximal ends of the arm portion manipulating wires 66 are attached; a pair of second supporting members 92 which are fixed so as to sandwich the second wire attachment plate 91, and are provided with a pair of columnar shaft members 92a which engages with the slits 88a of the second guide members 88. The second wire attachment plate 91, the pair of second supporting members 92, and the manipulation stick 82 constitute an oscillating body.

The second wire attachment plate 91, the pair of second supporting members 92 and the pair of second guide members 88 are formed, respectively so as to become symmetrical to the plane P2. A pair of holding mechanisms 300 are provided at the distal end of the second wire attachment plate 91 so as to become symmetrical to the axis C1 (especially refer to FIG. 5). In addition, although a detailed description is omitted, the holding mechanisms 300 are also similarly provided in the aforementioned first wire attachment plate 85.

Figure 6:
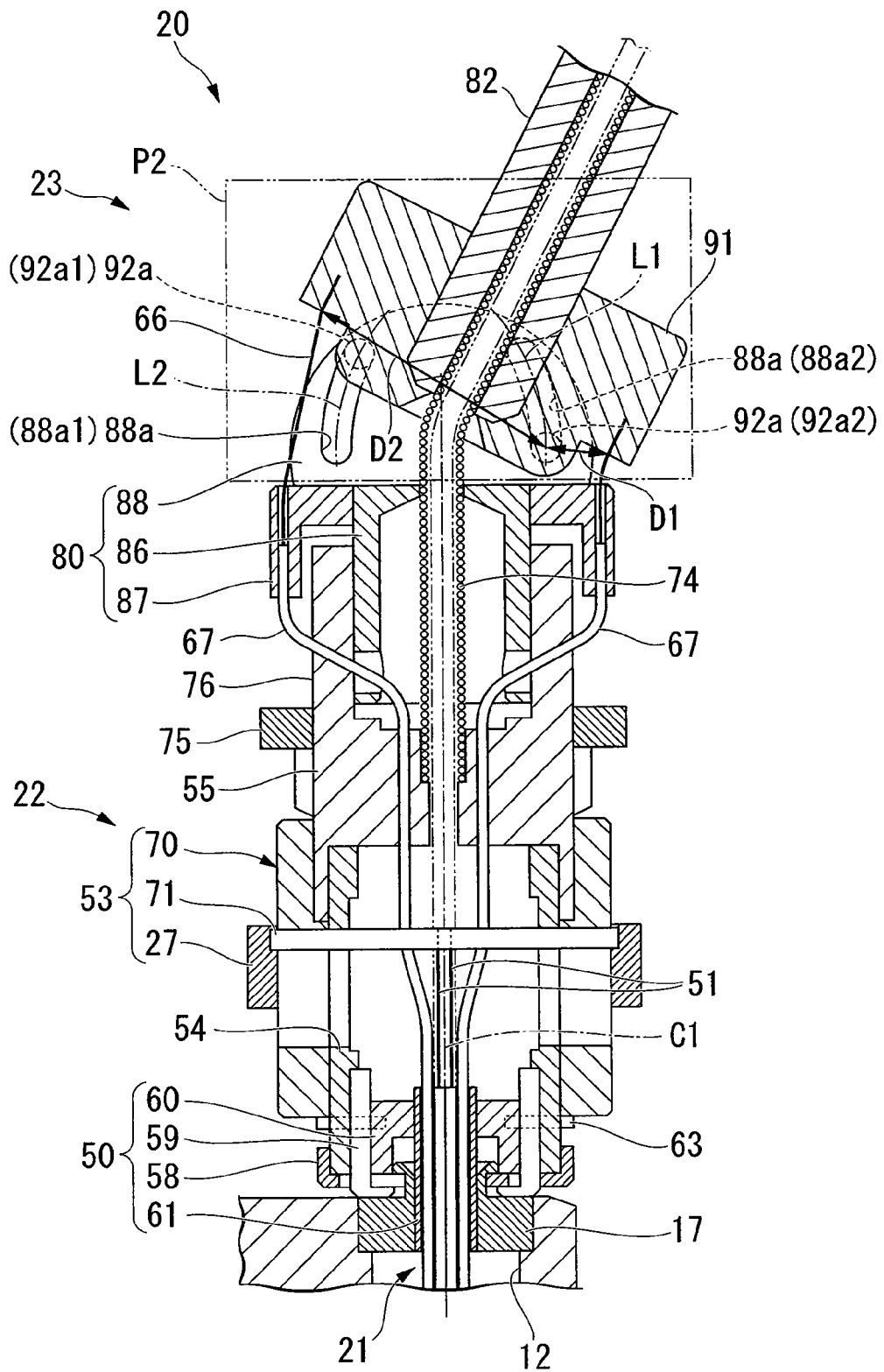
FIG. 6 is a sectional view around a holding mechanism of the arm mechanism.

As shown in FIG. 6, each holding mechanism 300 has a rod-shaped shaft 302 which is rotatably attached to the end of the second sheath attachment member 87 by a pin 301, and a holding portion 304 which is rotatably attached to the second wire attachment plate 91 by a pin 303, and slidably engages with the shaft 302.

Moreover, the holding portion 304 has a stopper case 307 where a cross-section by the plane P2 is formed substantially in the shape of the letter C, a stopper base 308 which is received within the stopper case 307, a plate-like stopper 309 which engages with the shaft 302, and a resilient member 310, such as a spring, which performs biasing so that the stopper base 308 and one end 309a of the stopper 309 are separated from each other.

The shaft 302 is arranged almost parallel to the axis C1. The shaft 302 and the stopper case 307 are configured so that each turns on the plane P2.

Both ends of the substantially C-shaped stopper case 307 are formed with through holes 307a and 307b, respectively, and the shaft 302 is inserted through the through holes 307a and 307b. In addition, an insertion hole 307c which extends to the distal end from an inner cavity of the stopper case 307 is formed at the axis C1 of the stopper case 307.

In the stopper base 308, a cross-section by the plane P2 is formed substantially in the shape of the letter E. The stopper base 308 is configured so that a first partition plate 308a arranged so as to be substantially orthogonal to the axis C1, a second partition plate 308b, and a third partition plate 308c are arranged in this order toward the proximal end from the distal end, and the ends thereof on the side of the axis C1 are integrally fixed to each other. The first partition plate 308a is set so as to extend longer in a direction away from the axis C1 than the second partition plate 308b and the third partition plate 308c, and the distal end of the first partition plate is formed with a through hole 308d through which the shaft 302 is inserted. The proximal ends of the arm portion manipulating wires 66 are attached to the first partition plate 308a of the stopper base 308. The gap between the second partition plate 308b and the third partition plate 308c is set to be greater than the thickness of the stopper 309.

As will be described later, when the arm manipulation portion 23 is operated, the stopper case 307 rotate about the pin 303 with respect to the shaft 302, or the stopper base 308 moves within the stopper case 307. However, even in this case, the internal diameters of the through holes 307a and 307b of the stopper case 307, and the through hole 308d of the stopper base 308 are set so as to allow free insertion of the shaft 302 through the through holes without being locked to the shaft 302.

Since a through hole 309b is formed at one end 309a of the stopper 309, the shaft 302 is inserted through the through hole 309b. Since the other end of the stopper 309 is arranged between the second partition plate 308b and third partition plate 308c of the stopper base 308, the aforementioned resilient member 310 is arranged between one end 309a of the stopper 309 and the first partition plate 308a of the stopper base 308. As one end 309a of the stopper 309 is biased toward the proximal end by the resilient member 310, an arrangement is made so that the other end of the stopper 309 is locked to the second partition plate 308b and the third partition plate 308c, and one end 309a is inclined toward the proximal end with respect to the other end of the stopper 309.

The internal diameter of the through hole 309b of the stopper 309 is set to be slightly greater than the external diameter of the shaft 302. Thus, when the stopper 309 is arranged at a position substantially orthogonal to the shaft 302, the shaft 302 is freely inserted through the through hole 309b, and when the stopper 309 is inclined at a predetermined angle or more from a position orthogonal to the shaft 302, the outer edge of the through hole 309b bites into the shaft 302, and thereby the stopper 309 bites into and is fixed to the shaft 302. That is, in FIG. 6, the proximal ends of the arm portion manipulating wires 66 are fixed to the second sheath attachment member 87.

Description will be continued referring back to FIGS. 3 to 5. Each arm portion manipulating wire 66 extends to the distal end of the arm portion 21 through one shaft member 92a or the other shaft member 92a.

Each shaft members of the pair of shaft members 92a is formed so as to be separated from each other and protrude from the second supporting members 92. As the pair of shaft members 92a engages with the slits 88a of the pair of second guide members 88, respectively, and the slits 88a guide the shaft members 92a, the second supporting members 92 are regulated so as to oscillate along the plane P2.

In addition, the pair of arm portion manipulating wires 66 for bending the first bending portion 43 of the arm portion 21 in two directions on one straight line with respect to the axis is attached to both ends of the first wire attachment plate 85, and the pair of arm portion manipulating wires 66 for bending the first bending portion 43 in two directions orthogonal to the two directions is attached to both ends of the second wire attachment plate 91. In addition, the positions of the first wire attachment plate 85 to which the proximal ends of the pair of arm portion manipulating wires 66 are attached move on the plane P1, respectively, and, the positions of the second wire attachment plate 91 to which the proximal ends of the pair of arm portion manipulating wires 66 are attached moves on the plane P2, respectively.

In addition, the other end of the spring member 74 which has one end fixed to the second main body member 55 passes between the pair of first supporting members 86 and between the pair of second supporting members 92, and is fixed to a through hole (oscillating-body-side channel) 82a which is coaxially formed in the manipulation stick 82 arranged on the axis C1. In this way, a channel 25 is formed including a through hole (insertion-part-side channel) 21a (refer to FIG. 2) formed in the arm portion 21, the inside of the first main body member 54, the inside of the second main body member 55, and the inner surface of the spring member 74, and the treatment tool 26 is inserted to the arm portion 21 through the inside of the channel 25.

As described hitherto, the relationship between the slits 76a of the first guide members 76 and the shaft members 86a of the first supporting members 86 which oscillate the first oscillating portion 80, and the relationship between the slits 88a of the second guide members 88 and the shaft members 92a of the second supporting members 92 which oscillate the second oscillating portion 81 have the same construction simply by making a rotation of 90 degrees as seen from the direction of the axis C1. That is, two sets having an oscillating body and a supporting body as one set are arranged in the arm manipulation portion 23 of the arm mechanism 20 of the present embodiment so that positions are shifted in the direction of the axis C1, and the plane P1 and the plane P2 on which the sets oscillate, respectively, are made to be orthogonal to each other. An oscillating body by the first wire attachment plate 85 and the pair of first supporting members 86, and a supporting body by the second guide members 88 are integrated with each other.

Thus, the relationship between the slits 88a and the shaft members 92a will be described. In addition, for the convenience of description only during description, the pair of slits 88a and the shaft members 92a are classified into and designated by slits 88a1 and 88a2 and shaft members 92a1 and 92a2.

When the first bending portion 43 of the arm portion 21 has a shape along the center axis of the arm portion 21, as shown, mainly, in FIG. 5, a pair of shaft members 92a1 and 92a2, in a plan view as seen so as to be orthogonal to the plane P2, is arranged symmetrically to the axis C1 of the main body 22, and protrudes in a direction orthogonal to the plane P2.

Here, as shown in FIGS. 3 to 5, a manipulation reference plane P3 orthogonal to the axis C1 and passing through a central point (starting point) Q1 of the shaft member 92a1 and a central point (starting point) Q2 of the shaft member 92a2 is set. In addition, as shown in FIG. 3, planes (second imaginary plane) P4 are respectively set on the inner surfaces of the pair of second guide members 88.

At this time, the pair of planes P4 becomes parallel to the plane P2. And the pair of second guide members 88 is arranged on the planes P2, respectively.

In addition, the slit 88a1 is formed in the shape of a long hole which has the central point Q1 as one end and which extends toward the proximal end (one side) of the main body 22 on a circular arc L2 which passes through the position of the through hole with the shaft member 92a2 as a center. Similarly, the slit 88a2 is formed in the shape of a long hole which has the central point Q2 as one end and which extends toward the proximal end on a circular arc L1 which passes through the position of the through hole with the shaft member 92a1 as a center. Moreover, the first bending portion 43 of the arm portion 21 has a shape along the center axis. When the manipulation stick 82, the first oscillating portion 80 and the second oscillating portion 81 are arranged on the axis C1 of the main body 22 (the position of the manipulation stick 82 and so on is hereinafter referred to as a "neutral position"), a certain tension (tensile force) acts on the four arm portion manipulating wires 66, respectively, and the shaft member 92a1 and the shaft member 92a2 are configured so as to be located at one ends of the central point Q1 and the central point Q2, respectively.

In addition, as shown in FIG. 1, since the arm manipulation portion 23 is arranged in the vicinity of the switches 30 and angle knobs 31 of the endoscope manipulation portion 2, for example, one operator can operate the arm manipulation portion 23, the switches 30, angle knobs 31, etc. with his/her other hand while supporting the endoscope manipulation portion 2 with his/her one hand.

Next, the procedure of excising a target tissue, in a digestive tract for example, will be described with reference to the endoscope device 1 configured in this way. First, the endoscope inserting portion 3 is inserted into a patient's body from a patient's mouth while the front of the endoscope inserting portion 3 is illuminated by the illumination mechanism 5 and a situation ahead of the endoscope inserting portion 3 is confirmed by the observation mechanism 6 and the monitor 15. At this time, the endoscope inserting portion is inserted while an angle knob 31 is rotated and the third bending portion 32 of the endoscope inserting portion 3 is bent to the center axis C0 if necessary. At this time, the arm mechanisms 20 may not be inserted through the lumens 8 and 9.

As shown in FIG. 2, when it is confirmed with the monitor 15 that the distal end of the endoscope inserting portion 3 has reached the target tissue K, the position of the distal end of the endoscope inserting portion 3 is fixed, and the arm portions 21 in which the treatment tools 26 have been inserted through the first lumen 8 and the second lumen 9, are inserted, respectively. Then, the main bodies 22 of the arm mechanisms 20 are attached to the forceps inlets 12 and 13, respectively, by engaging the cap 17 of the forceps inlets 12 and 13 with the sliding members 58 of the engagement mechanisms 50. Then, each arm portion 21 protrudes by a certain length from the opening 4a of the side surface of the endoscope inserting portion 3.

Figure 7:
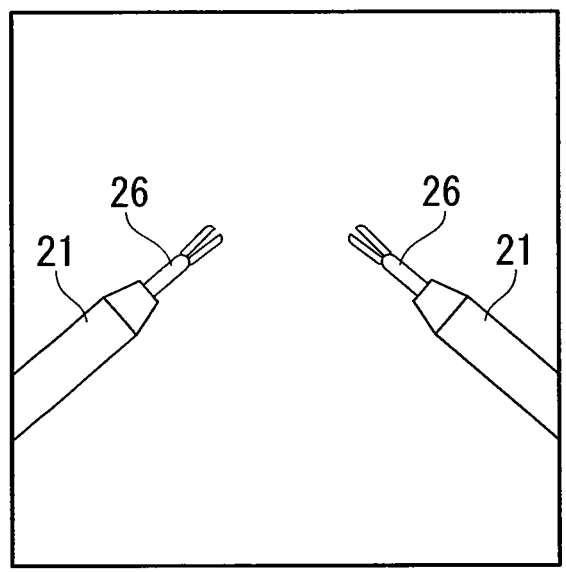
FIG. 7 is an explanatory view showing an image observed by a monitor of the endoscope device.

Here, by rotating the second bending manipulating ring 27 in the direction E1, the proximal ends of the pair of second bending manipulating wires 51 are pulled by the rod member 71, and the pair of second bending portions 42 is bent in the shape of the letter S facing each other, respectively, and is fixed. At this time, as shown in FIG. 7, as an image of the monitor 15, an arrangement of triangulation in which the distal ends of the treatment tools 26 approach each other, and the proximal ends of the arm portions 21 are separated from each other. As a result, the operation is easily performed.

In addition, in the present embodiment, the substantially circular hole 58a of the sliding member 58 of the main body 22 engages with the circular flange portion 17a of the cap 17. Thus, the direction in which the arm portion 21 is bent can be adjusted by rotating the main body 22 and arm manipulation portion 23 of the arm mechanism 20 about the axis C1 of the main body 22 with respect to each of the lumen 8 and 9. In addition, independently from this rotation, each treatment tool 26 can also be rotated around the axis thereof with respect to the arm mechanism 20. If necessary, an operator operates the manipulation stick 82 to adjust the direction in which the arm portion 21 is bent and the direction of the treatment tool 26 as will be described in detail later.

Next, the operator performs treatment of the target tissue K. First, in order to adjust the position and direction of the distal end of the arm portion 21 with the other hand while holding the endoscope manipulation portion 2 with one hand, the treatment tool 26 is advanced or retreated with respect to the manipulation stick 82 of one arm mechanism 20, or the manipulation stick 82 is oscillated with respect to the main body 22. When the treatment tool 26 is advanced or retreated with respect to the manipulation stick 82, the protrusion length of the treatment tool 26 from the distal end of the arm portion 21 is adjusted. Then, when the manipulation, stick 82 is oscillated with respect to the main body 22, the first bending portion 43 can be bent in four directions with respect to the center axis of the arm portion 21 as will be described below.

Figure 8:
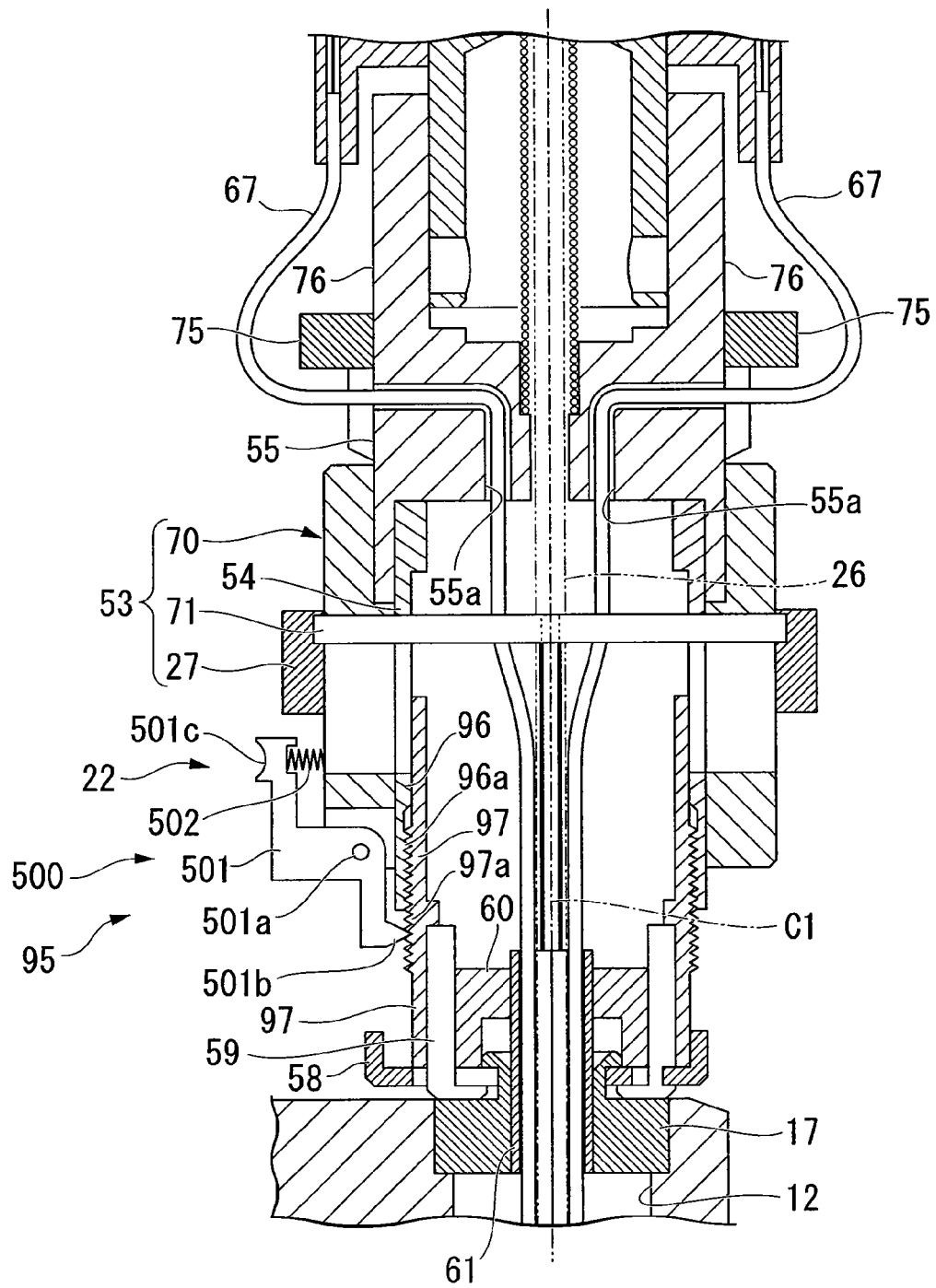
FIG. 8 is a sectional view showing the operation of main section of the arm mechanism.

That is, as shown in FIG. 8, for example, when the manipulation stick 82 of the arm mechanism 20 has been toppled toward the slit 88a1, the second wire attachment plate 91 rotates about the shaft member 92a1.

Figure 9:
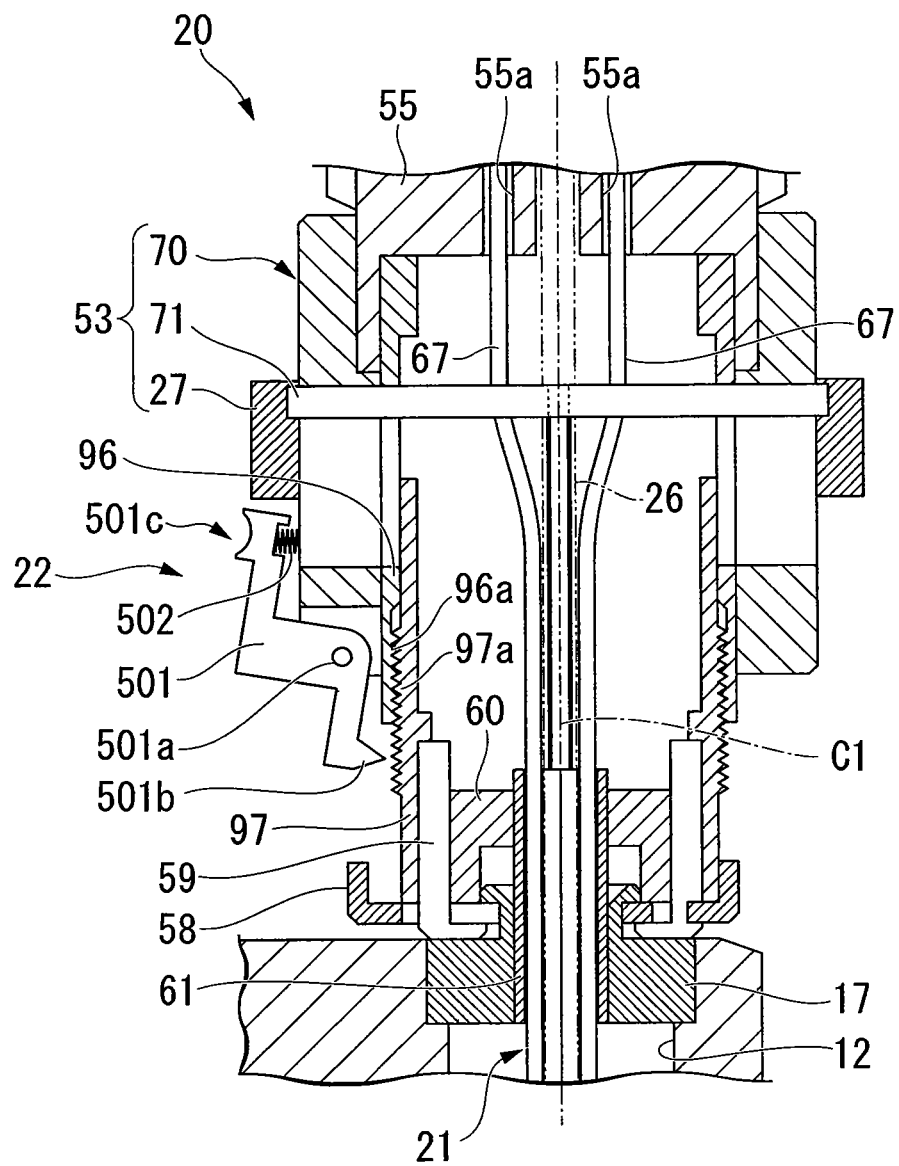
FIG. 9 is a sectional view showing the operation of the arm mechanism around the holding mechanism.

At this time, in the holding mechanism 300 provided at the slit 88a1, as shown in FIG. 9, the pin 303 along with the second wire attachment plate 91 rotationally moves in a direction indicated by an arrow in the drawing. Then, the inner surface of the distal end of the stopper case 307 abuts on the first partition plate 308a of the stopper base 308, and moves the stopper base 308 to the proximal end. For this reason, while the position of one end 309a of the stopper 309 is substantially maintained, the second partition plate 308b moves the other end of the stopper 309 to the proximal end, the stopper 309 becomes substantially orthogonal to the shaft 302, and the fixation between the shaft 302 and the stopper 309 is released.

When the operator releases his/her hand from the manipulation stick 82, the second wire attachment plate 91 is slightly inclined toward the slits 88a2 due to the difference between the tensions of the two arm portion manipulating wires 66 attached to the second wire attachment plate 91 (a pulled arm portion manipulating wire 66 has a stronger tension). Thereby, while the position of one end 309a of the stopper 309 is substantially held, the other end of the stopper 309 moves to the distal end, the outer edge of the through hole 309b bites into the shaft 302, and the stopper 309 is fixed to the shaft 302.

Then, as shown in FIG. 8, the arm portion manipulating wire 66 attached to the end of the second wire attachment plate 91 opposite to the side where the manipulation stick 82 has been toppled is pulled with the distance D1 as a radius from the center of the shaft member 92a1 to the position where the arm portion manipulating wire 66 is attached. For this reason, compared to the case where the second wire attachment plate 91 has rotated about an intermediate point between the shaft member 92a1 and the shaft member 92a2, the arm portion manipulating wire 66 can be pulled over a longer distance. On the other hand, the arm portion manipulating wire 66 attached to the end of the second wire attachment portion 91 on the side where the manipulation stick 82 has been toppled is pushed in with the distance D2 as a radius from the center of the shaft member 92a1 to the position where the arm portion manipulating wire 66 is attached. Thus, compared to the case where the second wire attachment plate 91 has rotated about the intermediate point, it is possible to reduce the amount of sagging of the arm portion manipulating wire 66.

Figure 10:
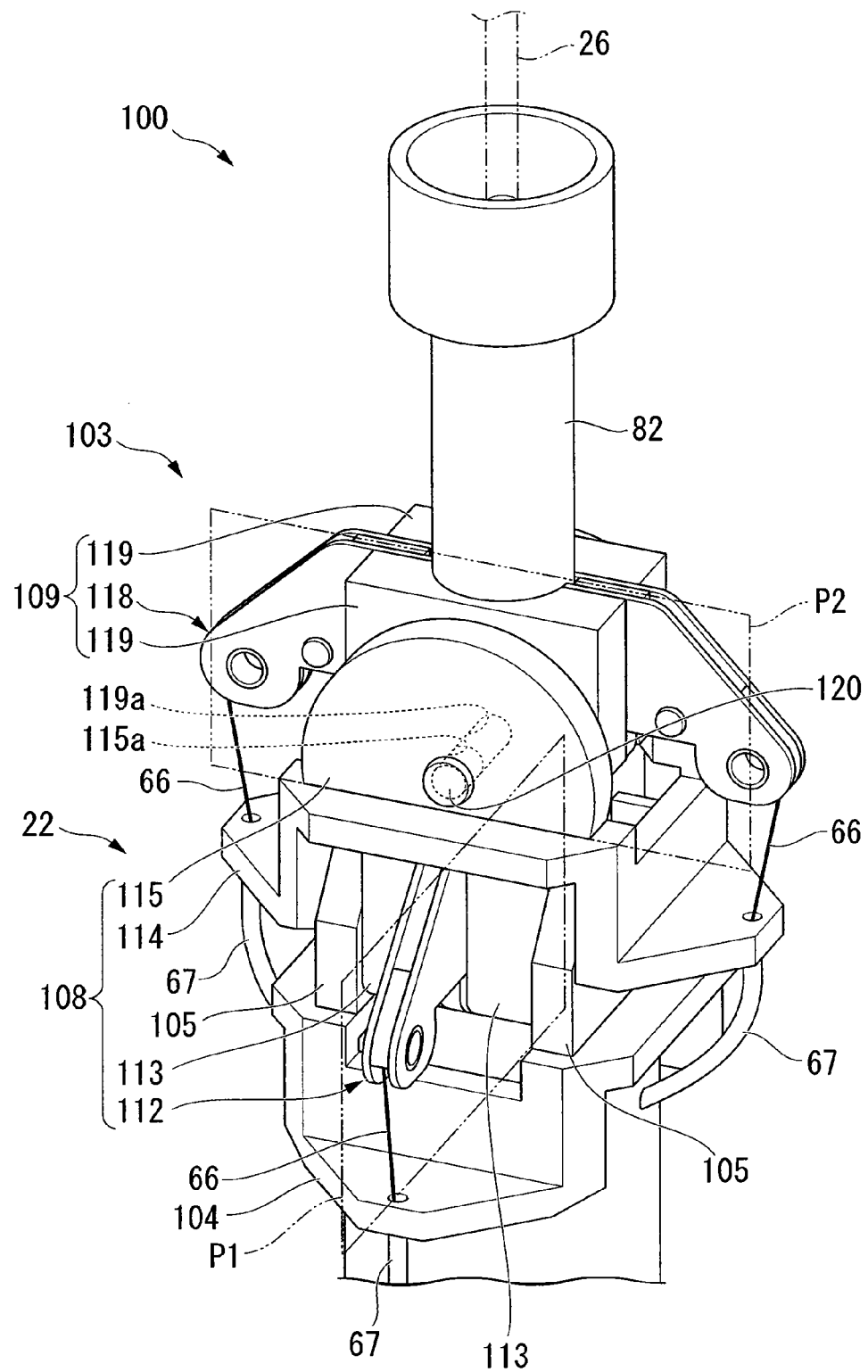
FIG. 10 is a sectional view showing the operation around the holding mechanism of the arm mechanism.

In addition, when the manipulation stick 82 has been toppled toward the slit 88a2 from this state, as shown in FIG. 10, the pin 303 along with the second wire attachment plate 91 rotationally moves in the direction indicated by the arrow in the drawing. Then, the inner surface of the proximal end of the stopper case 307 abuts one end 309a of the stopper 309, and as shown in FIG. 9, the portion of the stopper 309 nearer the proximal end than a plane P11 obtained by extending the surface of the third partition plate 308c at the proximal end is moved to the distal end. For this reason, as shown in FIG. 10, while the position of the other end of the stopper 309 is substantially maintained, the stopper case 307 moves one end 309a of the stopper 309 to the distal end, the stopper 309 becomes substantially orthogonal to the shaft 302, and the fixation between the shaft 302 and the stopper 309 is released.

In this way, the second wire attachment plate 91 rotates about the shaft member 92a1.

In the present embodiment, since the treatment tool 26 is advanced or retreated with respect to the manipulation stick 82, the oscillating center of the manipulation stick 82 becomes a certain position in the direction of the axis C1 of the main body 22, irrespective of the advance or retreat of the treatment tool 26. That is, as shown in FIG. 1, even if the operating end is located at a position Z1 or a position Z2 by advancing or retreating the treatment tool 26, the position of the oscillating center Z3 of the treatment tool 26 does not change. Thus, there is a merit in that natural oscillation manipulation can be performed. However, when oscillation is made in a state in which the treatment tool 26 has been pulled out to the most proximal end, i.e., a state in which the operating end of the treatment tool 26 has been pulled to the furthest existence, there is a possibility in that the moving range of the operating end of the treatment tool 26 becomes large, and interference with an operator or the endoscope manipulation portion 2 occurs.

In addition, in the present embodiment, the first bending portion 43 of the arm portion 21 has a shape along the center axis of the arm portion 21 when the manipulation stick 82 has been located at the neutral position. Thus, the position of the manipulation stick 82 corresponding to a state in which the first bending portion 43 becomes straight can be easily determined. When the first bending portion 43 of each arm portion 21 has a shape along the center axis, and the first oscillating portion 80 and the second oscillating portion 81 are arranged at positions along the axis C1 of the main body 22, a certain tension acts on the four arm portion manipulating wires 66, respectively. For this reason, the first bending portion 43 of the arm portion 21 is easily stabilized at a position along the center axis, and the manipulation stick 82 is easily stabilized at the neutral position.

Then, the operator operates the proximal end of the treatment tool 26 to grip and pull the target tissue K in the distal end of the treatment tool 26, and makes one arm mechanism 20 hold in the state. In addition, the operator operates the other arm mechanism 20 similarly to excises the target tissue K using the treatment tool 26.

In the present embodiment, as shown in FIG. 2, by projecting each arm portion 21 to the front from the endoscope inserting portion 3, and bending the respective second bending portion 42 and a first bending portion 43, the length A3 from the distal end of the treatment tool 26 to the distal end surface 3a of the endoscope inserting portion 3 can be shortened, and treatment can be performed even, for example, within a relatively narrow space within a digestive tract.

In this way, according to the arm manipulation portion 23 of the present embodiment, the pair of shaft members 92a respectively moves within the pair of slits 88a formed on the planes P4 of the second guide members 88. For this reason, the manipulation stick 82 which moves on the plane P2 parallel to the planes P4 can be stably oscillated along the slits 88a.

In addition, in the arm manipulation portion 23, switching is made such that, on the plane P2, the manipulation stick 82 oscillates around the central point Q1 as the shaft member 92a1 rotates around the central point Q1 of the slit 88a1 and the shaft member 92a2 moves within the slit 88a2, and the manipulation stick 82 oscillates around the central point Q2 as the shaft member 92a2 rotates around the central point Q2 of the slit 88a2 and the shaft member 92a1 moves within the slit 88a1. Accordingly, the oscillation of the manipulation stick 82 can be further stabilized.

When the manipulation stick 82 is inclined to one side from the neutral position, the oscillating center of the manipulation stick 82 can be kept from changing from either the shaft member 92a1 or the shaft member 92a2 to the other, and the operability of the manipulation stick 82 can be further improved.

In addition, the manipulation stick 82 can be more stably oscillated on the plane P2 by adopting an arrangement so that the manipulation stick 82 is sandwiched by the pair of second guide members 88.

In addition, two sets having an oscillating body and a supporting body as one set are arranged in the arm manipulation portion 23 so that the planes on which the sets oscillate, respectively, are orthogonal to each other. Thus, the manipulation stick 82 can be oscillated in two directions orthogonal to each other.

According to the arm mechanism 20 of the present embodiment, an arm portion manipulating wire 66 to be pulled can be switched, and the direction in which the first bending portion 43 is bent can be switched, by oscillating the manipulation stick 82 on the plane P2 around the position Q1 or around the position Q2.

In addition, since a certain tension acts on the arm portion manipulating wire 66 in the neutral position, when an external force is not applied to the manipulation stick 82, the manipulation stick 82 is located on the axis C1 of the main body 22. At this time, the shaft member 92a1 is arranged on the central point Q1 of the slit 88a1, and the shaft member 92a2 is arranged on the central point Q2 of the slit 88a2. Accordingly, the oscillating center of the manipulation stick 82 can be easily switched.

In addition, since the through hole 82a of the manipulation stick 8 and the through hole 21a of the arm portion 21 communicate with each other to constitute the channel 25, a treatment can be performed by inserting the treatment tool 26 through the channel 25 of the arm mechanism 20.

In addition, by inserting the arm mechanism 20 through each of the first lumen 8 and second lumen 9 formed in the endoscope device 1, and projecting the arm portion 21 through which the treatment tool 26 has been inserted from the distal end of each of the lumens 8 and 9, it is possible to perform various treatments using the treatment tool 26 while the first bending portion 43 of the arm mechanism 20 is bent.

In addition, the endoscope device 1 and the arm mechanism 20 can be integrated with each other, and the operability can be improved, by mounting the arm mechanism 20 on the endoscope device 1 in a state in which the arm portion 21 has been inserted through the first lumen 8 or the second lumen 9.

In addition, the workability of a treatment by the endoscope device 1 can be improved by rotating the arm portion 21 of the arm mechanism 20 around its own axis at the distal ends of the first lumen 8 and the second lumen 9.

Since the first wire attachment plate 85 and the second wire attachment plate 91 are provided with the holding mechanisms 300, the first bending portion 43 of the arm mechanism 20 can be easily bent, and the bending state of the first bending portion 43 bent by the operator can be maintained. It also becomes easy for one operator to operate the endoscope device 1.

In addition, the endoscope device 1 of the present embodiment can perform complicated treatments because two arm mechanisms 20 are used as described hitherto. In addition, as in a modified example shown in FIG. 11, each first main body member 54 in the present embodiment may be configured as a double pipe by a main body proximal end member 96 and a main body distal end member 97 which are substantially cylindrical and have different diameters, and positioning portions 96a and 97a which determine relative positions in the direction of the axis C1 direction may be provided on the inner peripheral surface of the main body proximal end member 96 and the outer peripheral surface of the main body distal end member 97 which abut each other. In the present modified example, the positioning portions 96a and 97a are formed in concavo-convex shape which continue in the direction of the axis C1 and which fit to each other.

The arm portion operating sheaths 67 are respectively inserted through through holes 55a formed in the second main body member 55.

In addition, a fixing mechanism 500 for fixing the main body proximal end member 96 to the main body distal end member 97 in the direction of the axis C1 is attached to the main body proximal end member 96. The fixing mechanism 500 has a lever 501 which is rotatably attached to the main body proximal end member 96 by a pin 501a, and a biasing member 502 which biases the lever 501 around the pin 501a. The lever 501 is provided with a claw portion 501b, and the claw portion 501b are enabled to fit to the positioning portion 96a of the main body proximal end member 96. In addition, the lever 501 is biased by the biasing member 502 so that the claw portion 501b fits to the positioning portion 96a.

The main body proximal end member 96, the main body distal end member 97, and the fixing mechanism 500 constitute a length adjusting mechanism 95.

Figure 11:
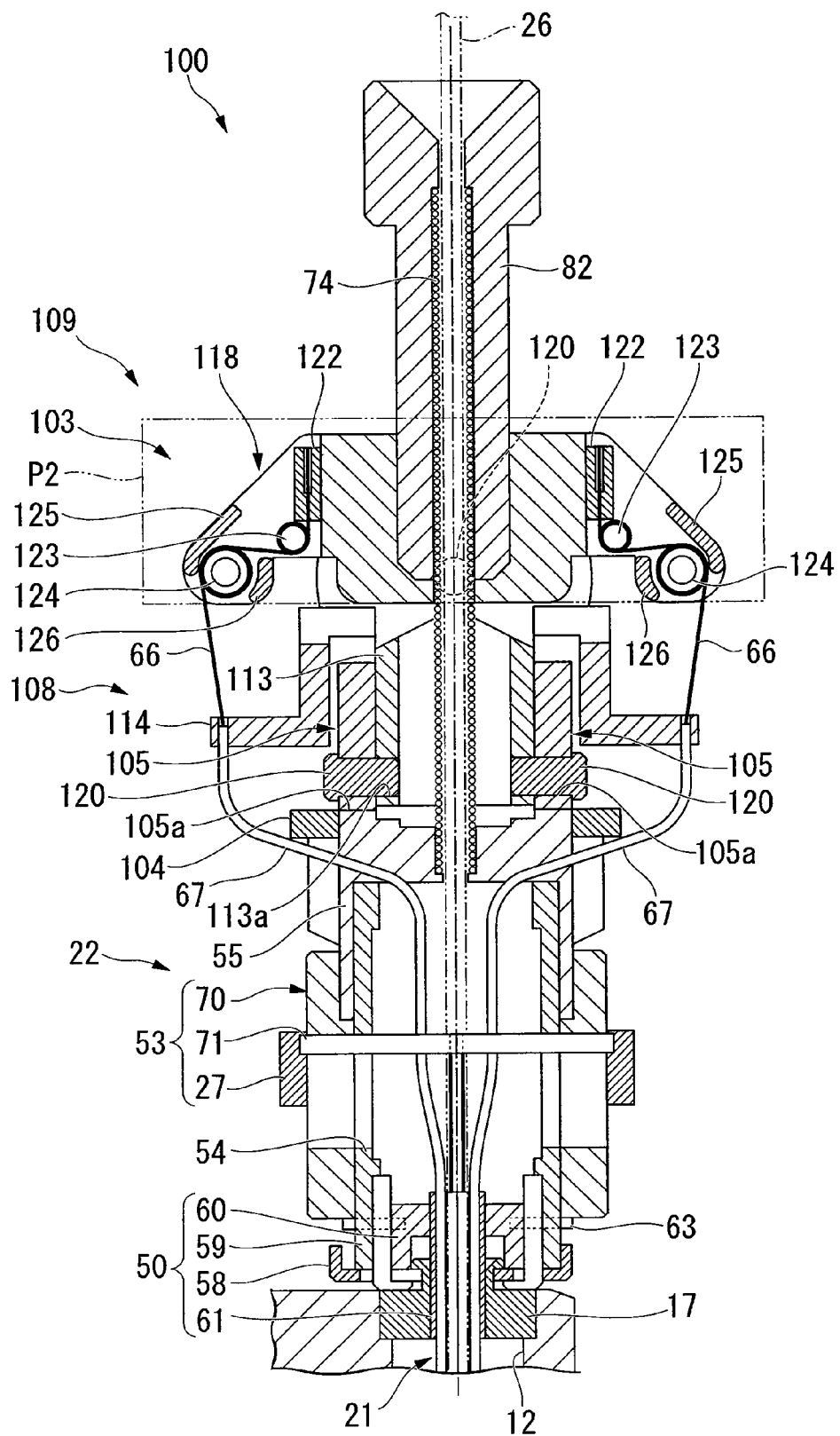
FIG. 11 is a sectional view of main section of an arm mechanism of a modified example of the first embodiment of the present invention.
Figure 12:
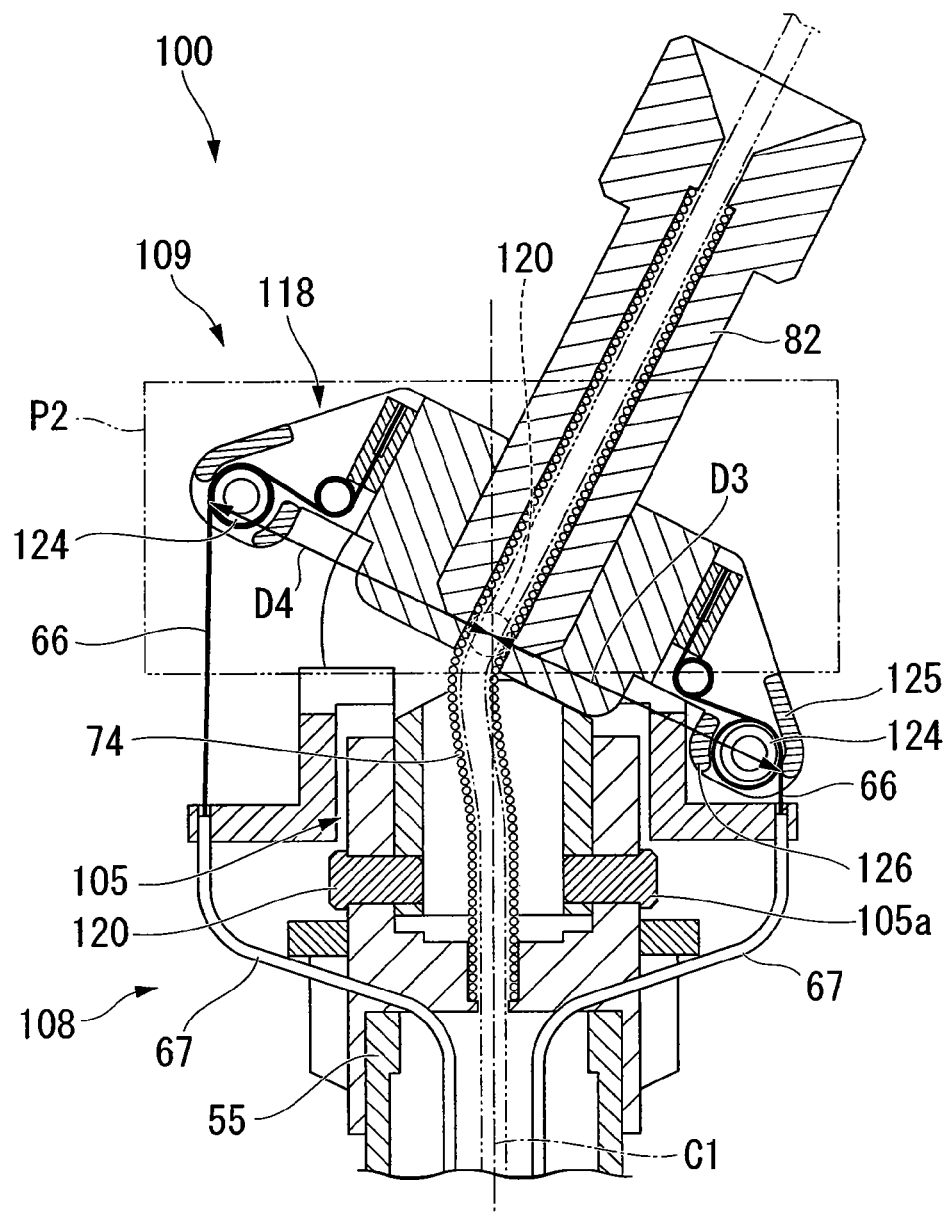
FIG. 12 is a sectional view showing the operation of the arm mechanism of the modified example.

FIG. 11 shows a state in which the main body proximal end member 96 has been fixed to the main body distal end member 97 in the direction of the axis C1. By pushing in a lever push portion 501c formed in the lever 501 toward the axis C1 against the force of the biasing member 502, the claw portion 501b and the positioning portion 96a can be separated from each other as shown in FIG. 12. The protrusion length of the treatment tool 26 can be changed by advancing or retreating the main body proximal end member 96 in the direction of the axis C1 in this state.

In addition, since the arm portion operating sheaths 67 are inserted through the through holes 55a formed in the second main body member 55, and allowance is given to the length, even if the main body proximal end member 96 is advanced or retreated with respect to the main body distal end member 97, the arm portion operating sheaths 67 can be prevented from extending.

In the present modified example, the length of the main body 22 of the arm mechanism 20 in the direction of the axis C1 can be adjusted, so that the protrusion length of the treatment tool 26 from the distal end of the arm portion 21 can be adjusted by the positional relationship between the main body proximal end member 96 and the main body distal end member 97, without changing the protrusion length of the treatment tool 26 closer to the proximal end than the manipulation stick 82 as in the first embodiment.

Figure 13:
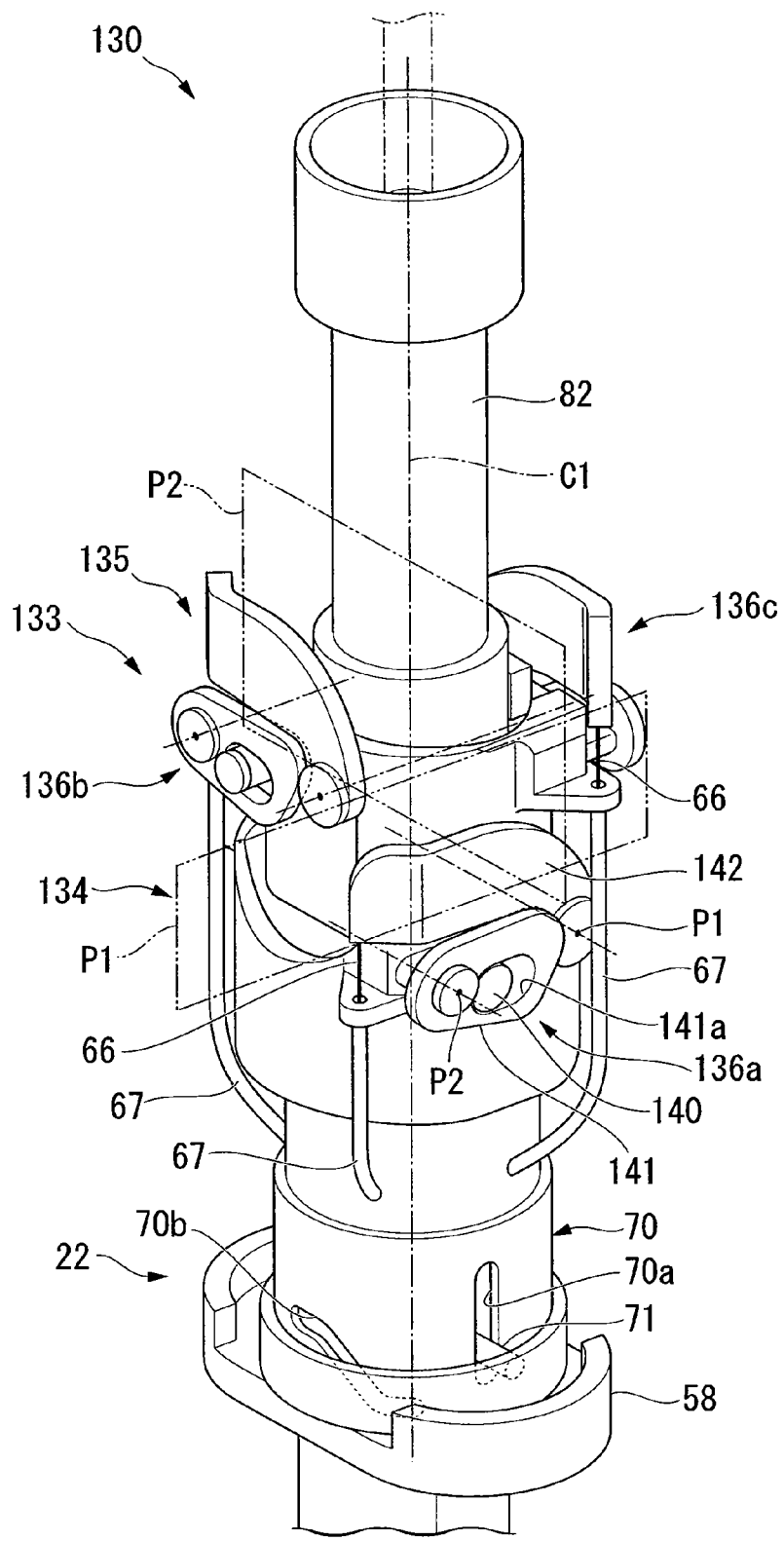
FIG. 13 is an overall view showing an endoscope device in a modified example.

In addition, since the oscillating center of the manipulation stick 82 itself advances or retreats in the direction of the axis C1, as shown in FIG. 13, the width of movement orthogonal to the direction of the axis C1 of the operating end of the treatment tools 26 can be kept constant irrespectively of the state of advance or retreat of the treatment tool 26, even if the operating end is located at a position Z4 or at a position Z5.

However, since the position of the oscillating center shifts due to the advance or retreat of the treatment tool 26, there is a possibility that an uncomfortable feeling may occur in manipulation feeling.

In addition, in the present modified example even in a case where the main body proximal end member 96 has rotated around an axis C1 with respect to the main body distal end member 97, the rotation is absorbed between the engagement mechanism 50 and the forceps inlet 12, and thereby, the arm mechanism 20 does not rotate.

In addition, even if the arm mechanism 20 moves in the direction of the axis C1, since allowance is given to the length of the manipulating wires 66 and the arm portion operating sheaths 67, the lengths of both do not run short. At this time, if the arm portion 21 is fixed to the distal end of the endoscope inserting portion, the arm portion 21 is prevented from jumping out of the endoscope inserting portion distal end due to the sagging of the manipulating wires 66 and the arm portion operating sheaths 67.

In addition, in the present embodiment, the pair of slits 70a and the pair of slits 88a are formed in the shape of a circular arc which has a central point Q1, etc. as a center. However, the shape of the slits 88a is not limited thereto, and may be formed so that the slits approach each other as being separated from each other to the proximal end of the main body 22 from the plane P3. This is also the same in the slits 70a.

In addition, in the present embodiment, two sets including an oscillating body and a supporting body as one set are arranged in the arm manipulation portion 23. However, a set of an oscillating body and a supporting body may be arranged in the arm manipulation portion 23.

Second Embodiment

Next, although the second embodiment according to the present invention will be described, the description of the same parts as the above embodiment will be omitted by giving the same reference numerals thereto, and only points differing those stated above will be described.

Figure 14:
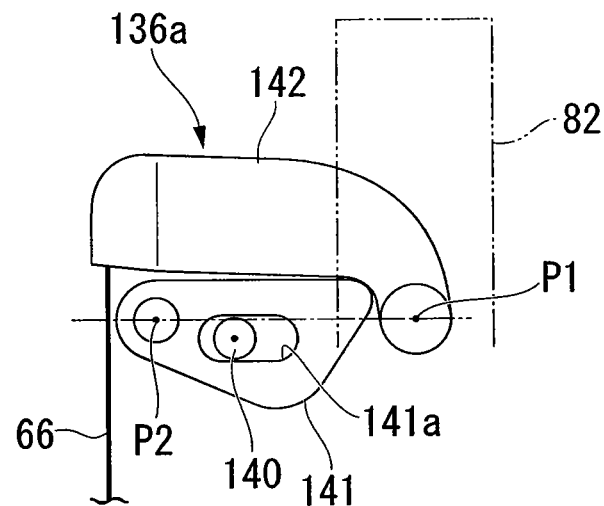
FIG. 14 is a perspective view of main section of an arm mechanism of an endoscope device in a second embodiment of the present invention.
Figure 15:
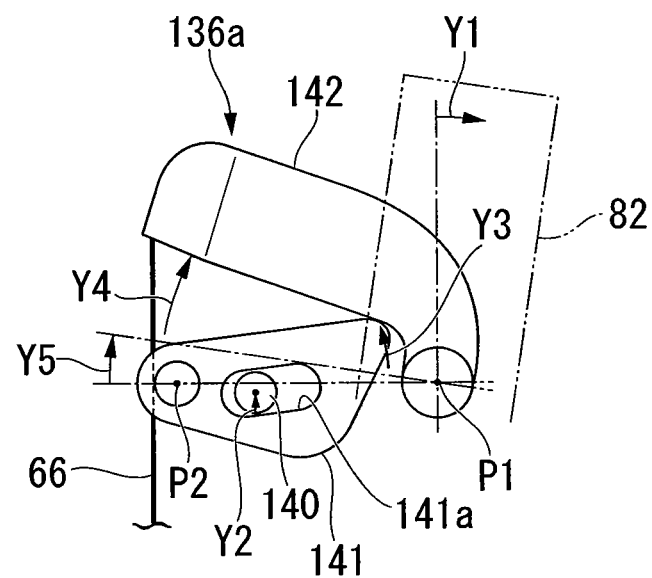
FIG. 15 is a sectional view of the main section of the arm mechanism.
Figure 16:
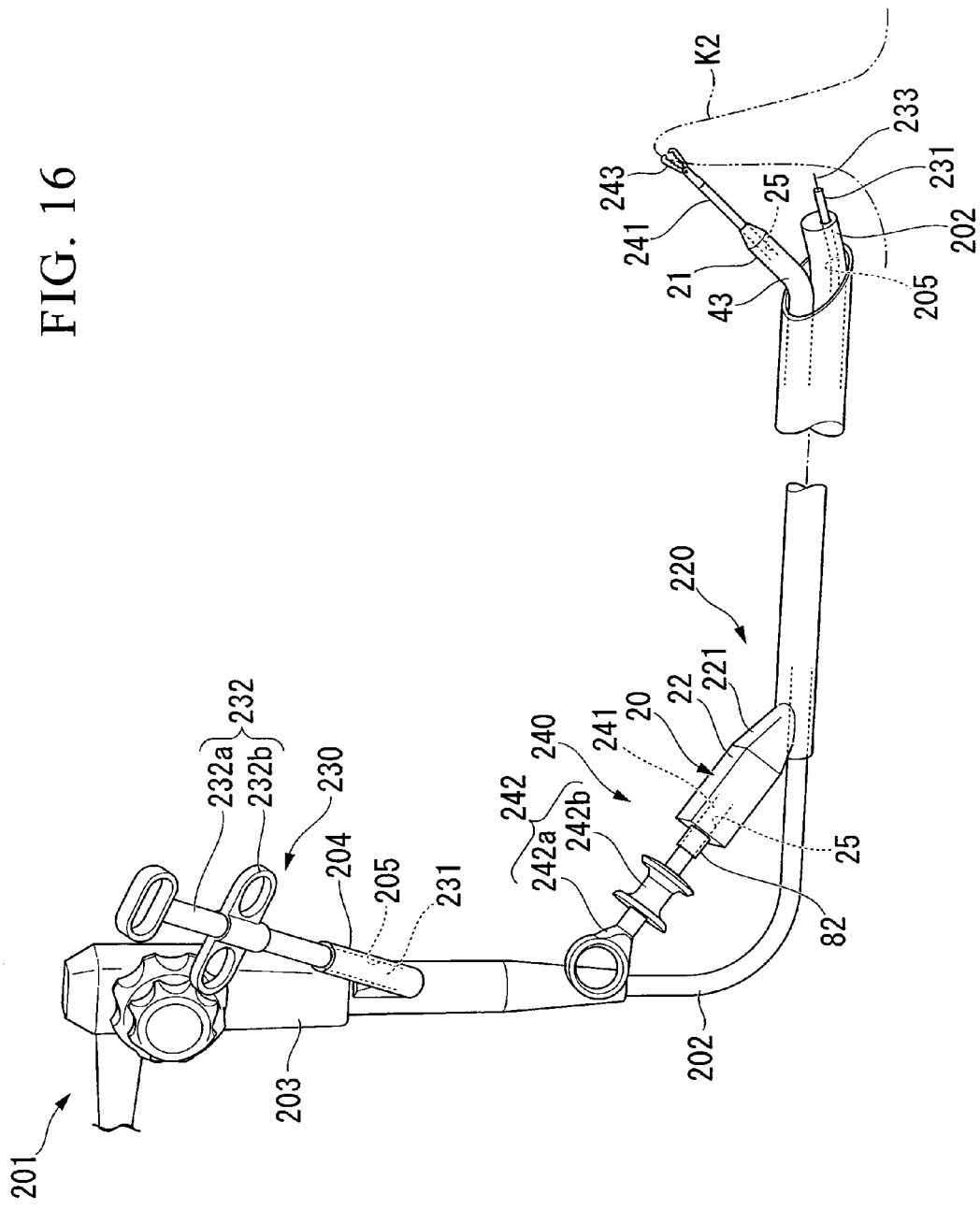
FIG. 16 is a sectional view showing the operation of the main section of the arm mechanism.

An arm mechanism 100 of the present embodiment, as shown in FIGS. 14 and 15, has the arm portion 21, the main body 22, and an arm manipulation portion 103 which operates the bending of the distal end of the arm portion 21.

The second main body member 55 of the main body 22 is provided with the spring member 74, a first sheath attachment member 104 arranged on the outer peripheral surface of the proximal end of the second main body member 55, and a pair of plate-like first guide members 105 which are arranged at the surface of the second main body member 55 at the proximal end to rotatably support a first oscillating portion 108 which is formed with through holes 105a, and will be described later.

The pair of arm portion operating sheaths 67 through which the arm portion manipulating wires 66 are inserted are attached to both ends of the first sheath attachment member 104.

In addition, the arm manipulation portion 103 includes the first oscillating portion 108 which is rotatably supported by the pair of first guide members 105 and oscillates on the plane P1 including the axis C1, a second oscillating portion 109 which is connected to the first oscillating portion 108 and oscillates on the plane P2 orthogonal to the plane P1 including the axis C1, and the cylindrical manipulation stick 82 which is fixed to the second oscillating portion 109.

The first oscillating portion 108 is provided with a plate-like first wire attachment portion 112 to which both ends of the proximal ends of the arm portion manipulating wires 66 are attached, a pair of first supporting members 113 which are fixed so as to sandwich the first wire attachment portion 112, a second sheath attachment member 114 which is arranged on the outer peripheral surfaces of the proximal ends of the pair of first supporting members 113 and has a pair of arm portion operating sheaths 67 attached thereto, and a pair of plate-like second guide members 115 which are arranged on the surfaces of the pair of first supporting members 113 at the proximal end to rotatably support the second oscillating portion 109 formed with the through hole 115a.

Each first supporting member 113 is formed with a through hole 113a communicating with the through hole 105a of each first guide member 105. In addition, the pair of arm portion operating sheaths 67 through which the arm portion manipulating wires 66 are inserted are attached to both ends of the second sheath attachment member 114.

A pair of pin members 120 are inserted through the through holes 105a of the first guide members 105 and the through holes 113a of the first supporting members 113, respectively, and the first oscillating portion 108 is rotatable with respect to the first guide members 105 about the pin members 120 on the plane P1.

The second oscillating portion 109 includes a plate-like second wire attachment portion 118 to both ends of which the proximal ends of the arm portion manipulating wires 66 are attached, and a pair of second supporting members 119 which are fixed so as to sandwich the second wire attachment portion 118, and is formed with through holes 119a communicating with the through holes 115a of the second guide members 115.

A pair of pin members 120 is inserted through the through holes 115a of the second guide members 115 and the through holes 119a of the second supporting members 119, respectively, and the second oscillating portion 109 is rotatable with respect to the second guide members 115 about the pin members 120 on the plane P2.

Here, since the configurations of the first wire attachment portion 112 and the second wire attachment portion 118 are the same, the configuration of the second wire attachment portion 118 will be described with reference to FIG. 15.

The second wire attachment portion 118 is provided with fixing members 122 which fix the proximal ends of the arm portion manipulating wires 66, first winding members 123 and second winding members 124 around which the arm portion manipulating wires 66 are wound, and regulating members 125 and 126 which prevents the arm portion manipulating wires 66 from jumping out to the outside. The arm portion manipulating wires 66 wound around the second winding members 124 respectively extend into the arm portion operating sheaths 67 attached to the second sheath attachment member 114.

In the arm mechanism 100 configured in this way, as shown in FIG. 12, for example, when the manipulation stick 82 of the arm mechanism 100 has been toppled along the second wire attachment portion 118, the second wire attachment portion 118 rotates on the plane P2 about the pin members 120. Then, the arm portion manipulating wire 66 attached to the end of the second wire attachment portion 118 opposite to the side where the manipulation stick 82 has been toppled is pulled with the distance D4 as a radius from the center of the pin member 120 to the position of the second winding member 124 where the arm portion manipulating wire 66 is paid out. On the other hand, the arm portion manipulating wire 66 attached to the end of the second wire attachment portion 118 on the side where the manipulation stick 82 has been toppled is pulled with the distance D3 as a radius from the center of the pin member 120 to the position of the second winding member 124 where the arm portion manipulating wire 66 is paid out. At this time, in the present embodiment, the space which receives the arm portion manipulating wire 66 remaining around the second winding member 124 is provided, it is possible to keep the arm portion manipulating wire 66 from sagging due to other parts, thereby operating the arm portion manipulating wire 66.

Third Embodiment

Figure 17:
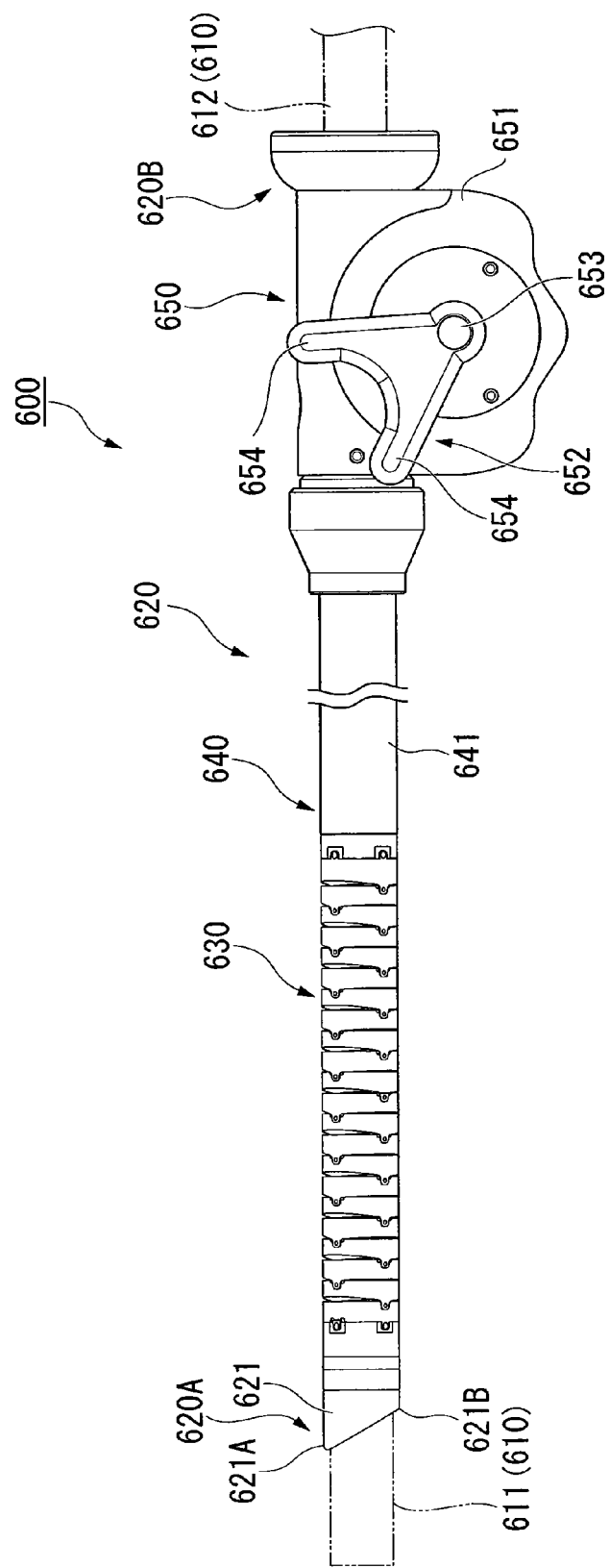
FIG. 17 is a view showing an overtube of a third embodiment of the present invention.

A medical system 600 including an manipulation mechanism and a medical instrument in a third embodiment of the present invention will be described below. FIG. 17 is a view showing the medical system 600.

As shown in FIG. 17, the medical system 600 includes an endoscope device 610 and an overtube (medical instrument) 620 used while being attached to the endoscope device 610.

In the present embodiment, a well-known endoscope can be appropriately employed as the endoscope device 610. For example, the endoscope device 610 of the present embodiment includes a tubular inserting portion 612, a distal end imaging part 611 provided at the distal end of the inserting portion 612, and a manipulation portion attached to the proximal end of the inserting portion 612 (not shown).

The overtube 620 is used as a guide tube when the endoscope device 610 is inserted into the body. The overtube 620 includes a bending operating portion 630 provided at a distal end 620A, a tubular inserting portion 640 which has one end fixed to the bending operating portion 630, and an manipulation portion 650 fixed to the other end of the inserting portion 640.

In addition, a soft member 621 is attached to the distal end 620A of the overtube 620. The soft member 621 is formed from rubber, etc., and prevents a tissue from being damaged at the distal end of the overtube 620 when the overtube 620 is inserted into a body cavity. The soft member 621 is formed in a tubular shape, and the distal end of the soft member 621 is cut obliquely with respect to the axis. Since the distal end of the soft member 621 is obliquely cut, the axial dimension of a first distal end 621A which is drawn near to the proximal end by a wire 656 which will be described later when the bending operating portion 630 is bent is made to be longer than the axial dimension of an opposite second distal end 621B.

Figure 18:
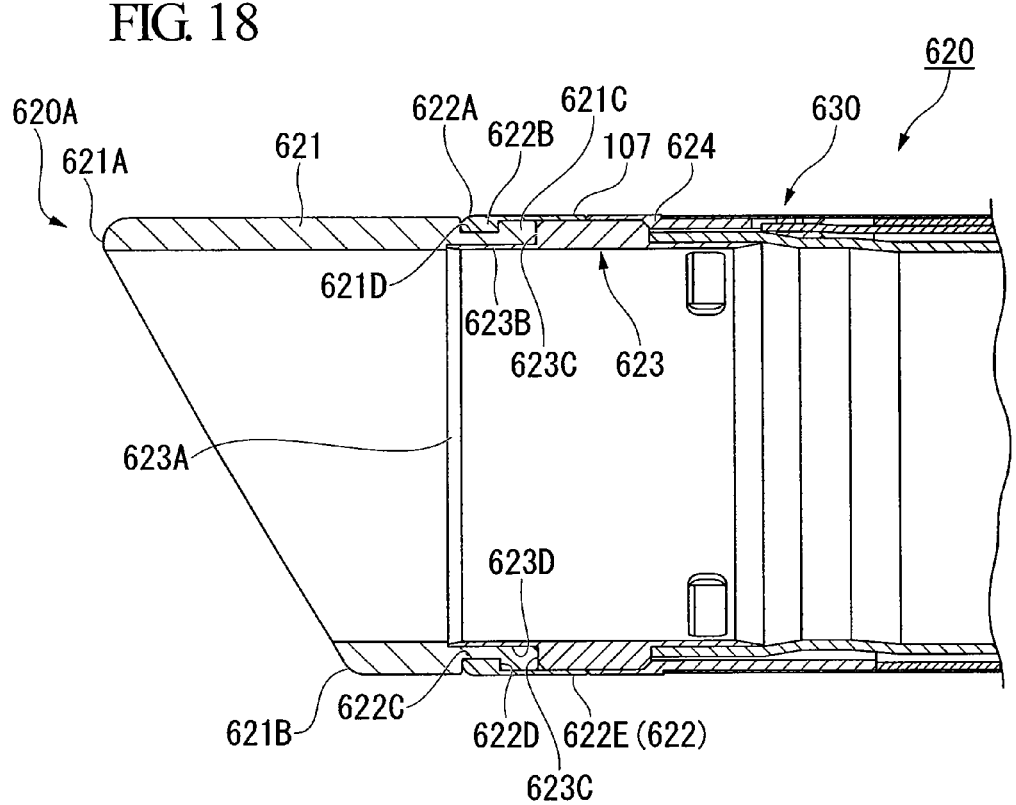
FIG. 18 is an enlarged sectional view showing a distal end of the overtube in an enlarged manner.

FIG. 18 is an enlarged sectional view showing a portion of the distal end 620A of the overtube 620 in an enlarged manner. As shown in FIG. 18, a groove 621D is provided along the circumferential direction in the outer surface of the soft member 621 on the side of the proximal end 621C. The soft member 621 is fixed to the distal end of the bending operating portion 630 by a first fixing portion 622 and a second fixing portion 623.

The first fixing portion 622 is formed in a tubular shape. A fitting portion 622B fitted to the groove 621D of the soft member 621 is formed at a distal end 622A of the first fixing portion 622. A female thread which is screw-fitted to the second fixing portion 623 is formed in the inner surface of the first fixing portion 622 on the side of the proximal end 622E.

The second fixing portion 623 is formed in a tubular shape, and the proximal end 622E of the first fixing portion 622 is screw-fitted to the outer surface of the second fixing portion 623. A small diameter portion 623B in contact with the inner wall surface of the soft member 621 is formed at the distal end 623A of the second fixing portion 623. In addition, a proximal end of the small diameter portion 623B is formed with a stepped surface 623C which extends in the direction of a plane orthogonal to the axis of the second fixing portion 623. A proximal end of the second fixing portion 623 is fixed to the distal end of the bending operating portion 630.

The distal end 623A of the second fixing portion 623 is tapered so that the internal diameter thereof become gradually large as it goes toward the distal end 623A in the axial direction of the second fixing portion 623. By connecting the second fixing portion 623 and the soft member 621 together in a moderately inclined plane, the possibility that the inserting portion 612 of the endoscope device 610 is caught between the second fixing portion 623 and the soft member 621 can be reduced.

The proximal end 621C of the soft member 621 is sandwiched between the inner surface 622C of the fitting portion 622B formed in the first fixing portion 622, and the outer surface 623D of the small diameter portion 623B formed at the distal end 623A of the second fixing portion 623. In addition, the proximal end 621C of the soft member 621 is sandwiched between the stepped surface 622D located at the proximal end of the fitting portion 622B formed in the first fixing portion 622, and the stepped surface 623C formed in the second fixing portion 623. Accordingly, the soft member 621 is surely fixed to the distal end of the bending operating portion 630.

With the soft member 621 fixed, the distal end 623A of the second fixing member 623 is located ahead of the distal end 622A of the first fixing member 622, i.e., closer to the distal end 620A of the overtube 620. For this reason, even if the outer surface of the soft member 621 is pushed, the portion where the groove 621D is provided is hardly deformed radially inward, and a tissue can be prevented from being damaged by an exposure of the distal end 622A of the first fixing member. In addition, since the outer surface of the distal end 622A of the first fixing member 622 is worked in the shape of a curved surface, even if the distal end 622A of the first fixing portion 622 is exposed to the outside due to the deformation of the soft member 621, a tissue is hardly damaged.

Figure 19:
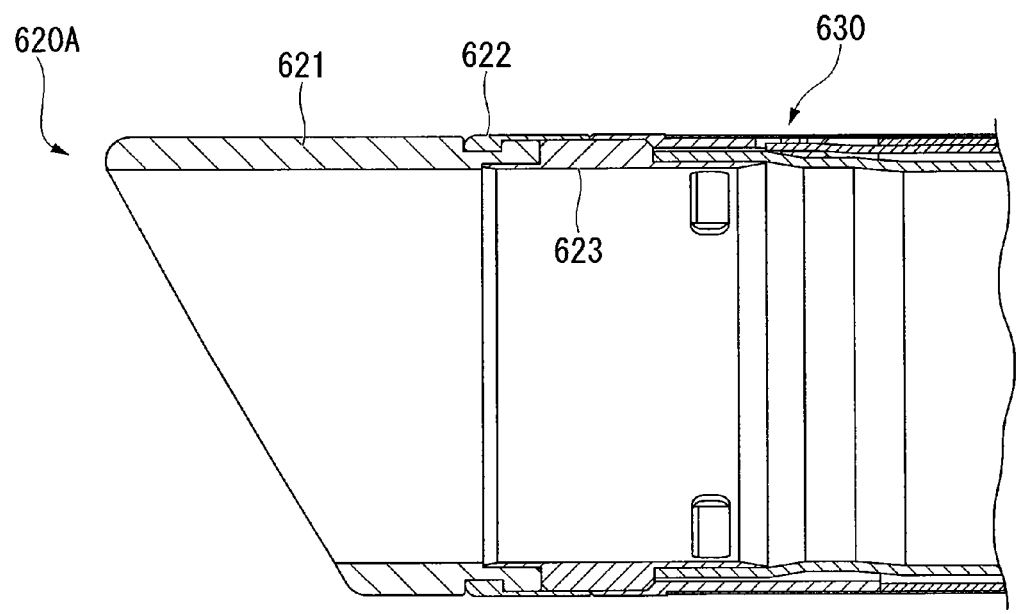
FIG. 19 is an enlarged sectional view showing a modified example of the distal end of the overtube.

In addition, as shown in FIG. 19, the dimensions or the like of respective members may be set so that the distal end 623A of the second fixing member 623 is located behind the distal end 622A of the first fixing member 622. Whether any forms are selected may be appropriately determined according to an endoscope to be inserted.

Figure 20:
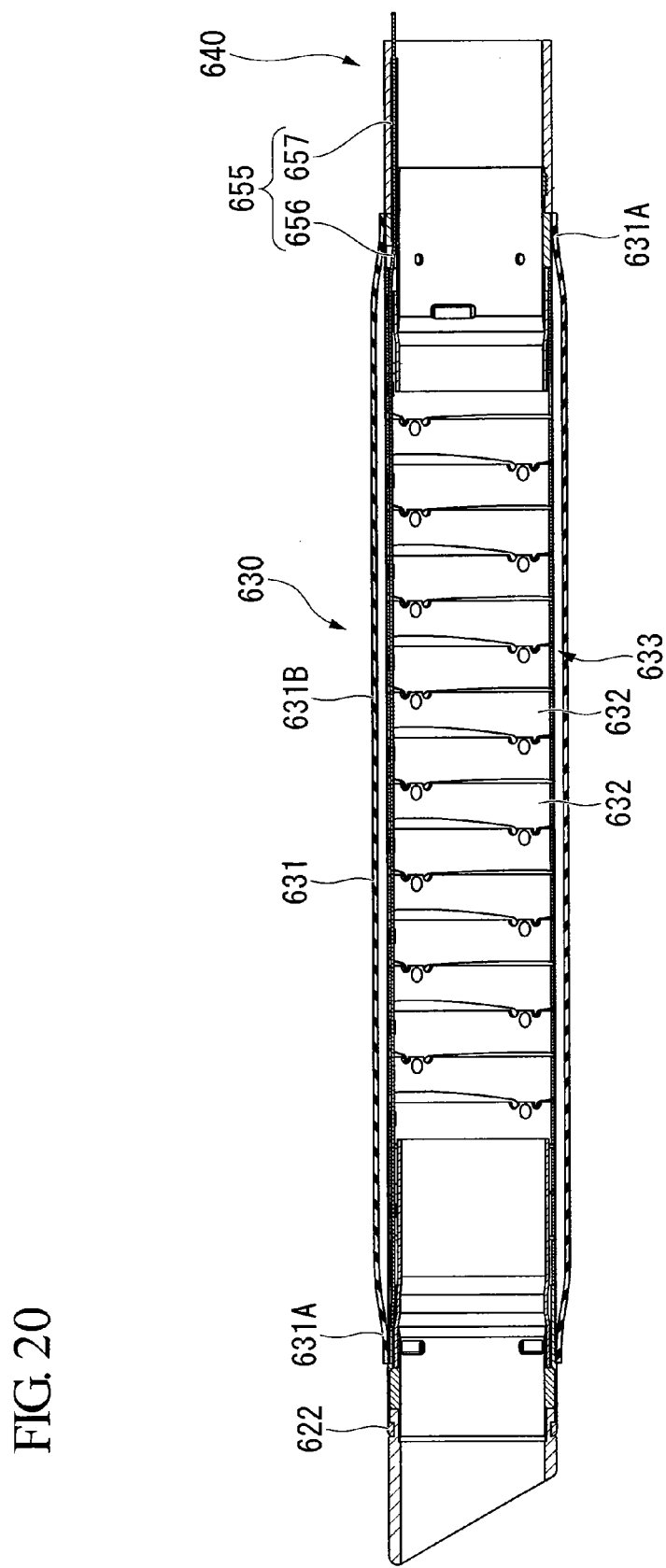
FIG. 20 is an enlarged sectional view showing a bending operating portion in the overtube in an enlarged manner.

FIG. 20 is an enlarged sectional view showing the bending operating portion 630 in the overtube 620 in an enlarged manner. As shown in FIG. 20, the bending operating portion 630 is arranged at the distal end of the inserting portion 640, and has a jacket layer 631 which covers the outer periphery of the bending operating portion 630, and a bending tube 633 which has a plurality of the bending pieces 632 which are lined up and connected together in the axial direction inside the jacket layer.

Figure 21:
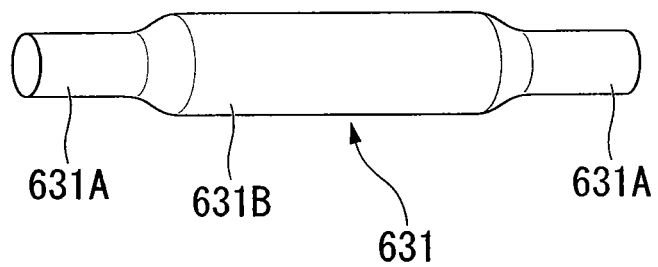
FIG. 21 is a view showing the shape of a jacket layer.

The jacket layer 631 which forms the outermost layer of the bending operating portion 630 is formed from a polyurethane tube with a thickness of about 0.1 mm. As shown in FIG. 21, the external diameter of an axial end 631A of the jacket layer 631 is small, and the internal diameter of an intermediate portion 631B sandwiched into the end 631A is about several millimeters greater than the end 631A. The size of the internal diameter of the jacket layer 631 at the end 631A is almost the same size as the external diameter of the first fixing member 622. By adopting such a shape, both ends 631A are brought into close contact with the first fixing member 622 without a gap, and are favorably bonded to the first fixing member, and the intermediate portion 631B covers the outside of the bending pieces 632 to favorably prevent the tissue damage caused by the bending pieces 632, while permitting the motion of the bending pieces 632 accompanying bending.

Figure 22:
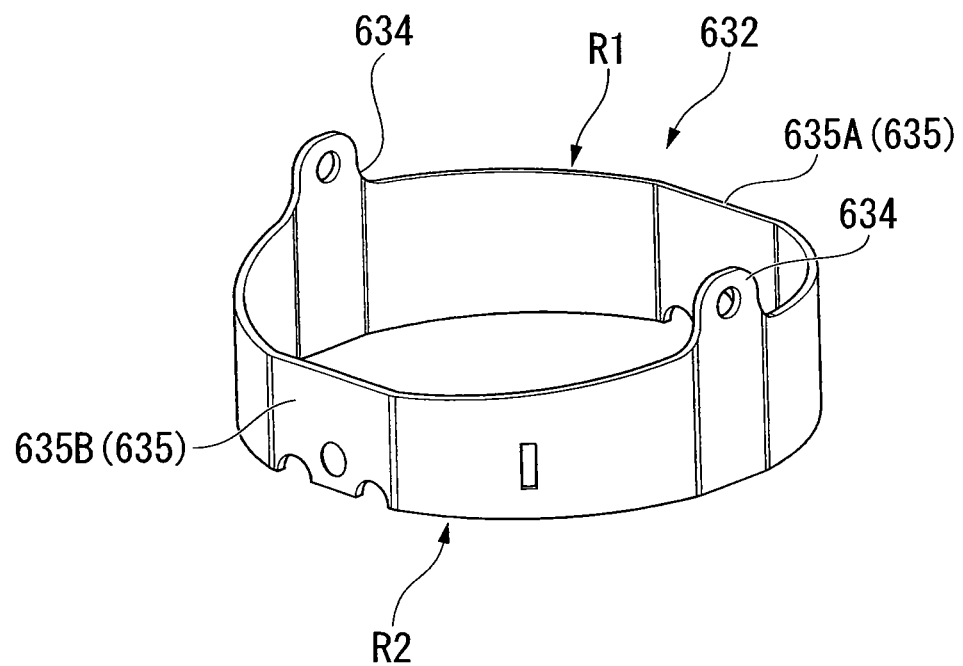
FIG. 22 is a perspective view showing a bending piece of the bending portion.
Figure 23:
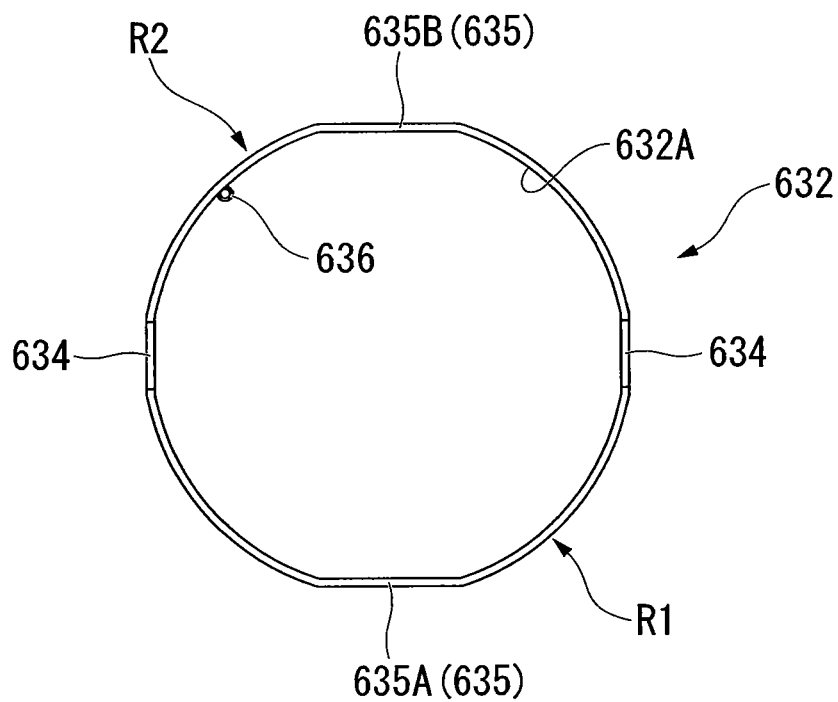
FIG. 23 is a view when the bending piece is seen from the axis direction.

FIG. 22 is a view showing a bending piece 632 attached to the bending operating portion 630. The bending piece 632 is formed from metal with a thickness of about 0.3 mm so that the internal diameter of the bending operating portion 630 can be guaranteed as largely as possible. As shown in FIG. 23, the bending piece 632 is formed so that the shape thereof seen from the axis direction is as close to a circle as possible. That is, although a connecting portion 634 connected to a bending piece at the distal end and a connected portion 635 connected to a bending piece at the proximal end are formed in a planar shape, the other portions are formed substantially in the shape of a circular arc which has the axis of the bending piece 632 as a center. A pair of connecting portions 634 is provided at radially facing positions of the bending piece 632. In addition, a pair of connected portion 635 is provided at positions which are different from the connecting portions 634 in the circumferential direction of the bending piece 632.

As shown in FIG. 22, a base portion where a portion of the connecting portion 634 protrudes in the axis direction is formed in the shape of a curve in order to prevent the concentration of stress. The end of the flat connecting portion 634 in the circumferential direction of the bending piece is formed so that the base portion of the connecting portion 634 comes into contact with the end surface of the bending piece 632 at the front end. In addition, the shape of the base portion of the connecting portion 634 may include a straight portion partially as long as the base portion is formed substantially in the shape of a curve so as not to have a corner where stress is concentrated. As the bending piece is formed in this way, the bending piece 632 can be formed so as to have sufficient strength while being formed from thin metal.

As the areas of the planar connecting portion 634 and connected portion 635 become smaller, the shape of the bending piece 632 in the radial direction becomes closer to a circle, and a larger inner cavity can be guaranteed. For this reason, it is preferable that the dimensions of the connecting portion 634 and the connected portion 635 in the circumferential direction of the bending piece be set to a range where the strength required for connection is held as small as possible. In the present embodiment, the width of the connecting portion 634 is 2.5 mm, and the diameter of an inscribed circle (almost the same as that of the effective internal diameter of the bending operating portion 630) of the bending piece 632 is φ15.7 mm.

Although the end surface of the bending piece 632 at the proximal end has a cross-section orthogonal to its own axis, the axial dimension of one connected portion (first connected portion) 635A of two connected portions 635 is longer than that of the other connected portion (a second connected portion) 635B, and protrudes further axially forward than the second connected portion 635B. Accordingly, the area of the outer peripheral surface of a first region R1 between the connecting portions 634 with the first connected portion 635A therebetween is greater than the area of the outer peripheral surface of a second region R2 between the connecting portions 634 with the second connected portion 635B therebetween.

Figure 24:
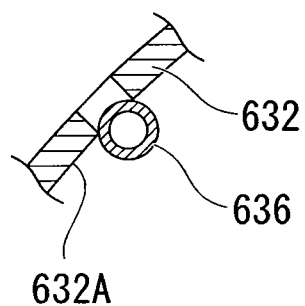
FIG. 24 is an enlarged sectional view of an insertion pipe provided in the bending piece.

An insertion pipe 636 through which a wire 656 which will be described later is inserted is fixed to each of the bending pieces 632. The insertion pipe 636 is attached to an inner surface at an intermediate position between the connecting portion 634 and the second connected portion 635B. As shown in FIG. 24 in an enlarged manner, the insertion pipe 636 is attached to the bending piece 632 by laser welding or brazing in a state in which a portion of the outer peripheral surface is buried in a through hole formed through the outer wall of the bending piece 632. For this reason, since the inner peripheral surface of the insertion pipe 636 is arranged so as to touch an imaginary inner peripheral surface of the bending piece 632, and the inner surface of the bending piece 632 and the inner surface of the insertion pipe 636 are smoothly continuous without a height difference, the wire 656 can be smoothly advanced or retreated, and the inner cavity of the bending operating portion 630 can be guaranteed more largely. In the present embodiment, the insertion pipe 636 is fixed to all the bending pieces 632 provided in the bending tube 633, and the wire 656 is inserted through all the insertion pipe 636. Thereby, since the wire 656 is deformed along the bending of the bending operating portion 630, it is possible to reduce the possibility of the wire 656 being excessively twisted.

Figure 25:
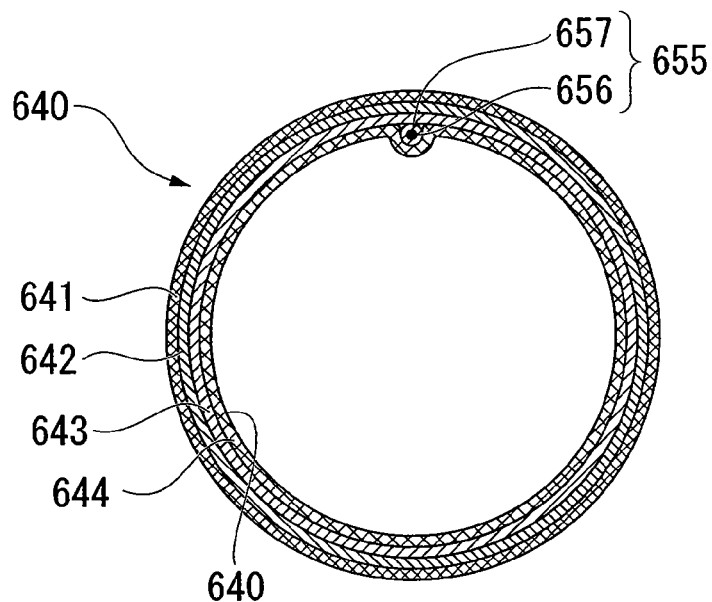
FIG. 25 is a sectional view when the inserting portion is seen in a cross-section orthogonal to an axial direction of the inserting portion of the overtube.

FIG. 25 is a cross-sectional view of the inserting portion 640 in a cross-section orthogonal to the axial direction of the inserting portion 640. As shown in FIG. 25, the inserting portion 640 is a multilayer tube in which an outer tube layer 641, a blade tube layer 642, a flexible layer 643, and an inner tube layer 644 are provided sequentially from the outside.

The outer tube layer 641 and the inner tube layer 644 are flexible resin tubes which are formed in a tubular shape.

The blade tube layer 642 is a tube in which a metal wire rod is knit in a direction orthogonal to the center axis of the inserting portion 640 and is formed in the shape of a tube.

The flexible layer 643 is formed such that a flat wire rod is spirally wound, and is formed in the shape of a long tube in the axial direction of the inserting portion 640. The shape of a cross-section orthogonal to the axial direction of the flat wire rod is a rectangular shape. The flexible layer 643 has elasticity, and is straight in a natural state.

A transmission portion 655 connected to each of the manipulation portion 650 and the bending operating portion 630 is arranged between the flexible layer 643 and the inner tube layer 644.

The transmission portion 655 has a wire 656 the distal end of which is fixed to the distal end 630A of the bending operating portion 630, and a tubular coiled tube 657 through which the wire 656 is inserted so as to be able to advance or retreat.

The wire 656 is provided to transmit operator's manipulation input in a handle portion 654 of the manipulation portion 650, which will be described later, to the bending operating portion 630. The shape of the wire 656 is linear, and the cross-sectional shape of the wire orthogonal to the axial direction is a circular shape. In addition, a proximal end 656B of the wire 656 is fixed to the inside of a pulley 660 provided in the manipulation portion 650 which will be described later. The material of the wire 656 is preferably a material with strength such that the wire 656 is not broken when the bending operating portion 630 is bent. In addition, the tensile strength may be increased by adopting a knit wire as the wire 656. As the material of the wire 656, carbon fibers, resin fibers, metal wire rods, and so on can be employed.

Figure 26:
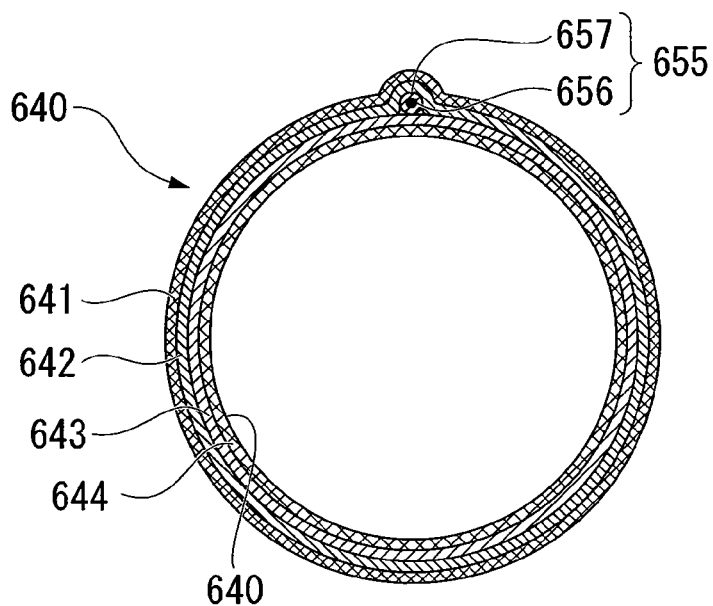
FIG. 26 is a view showing another example of a configuration of the inserting portion of the overtube.

FIG. 26 is a view showing another configuration example of the inserting portion 640. As shown in FIG. 26, the transmission portion 655 may be provided between the blade tube layer 642 and the flexible layer 643.

Figure 27A:
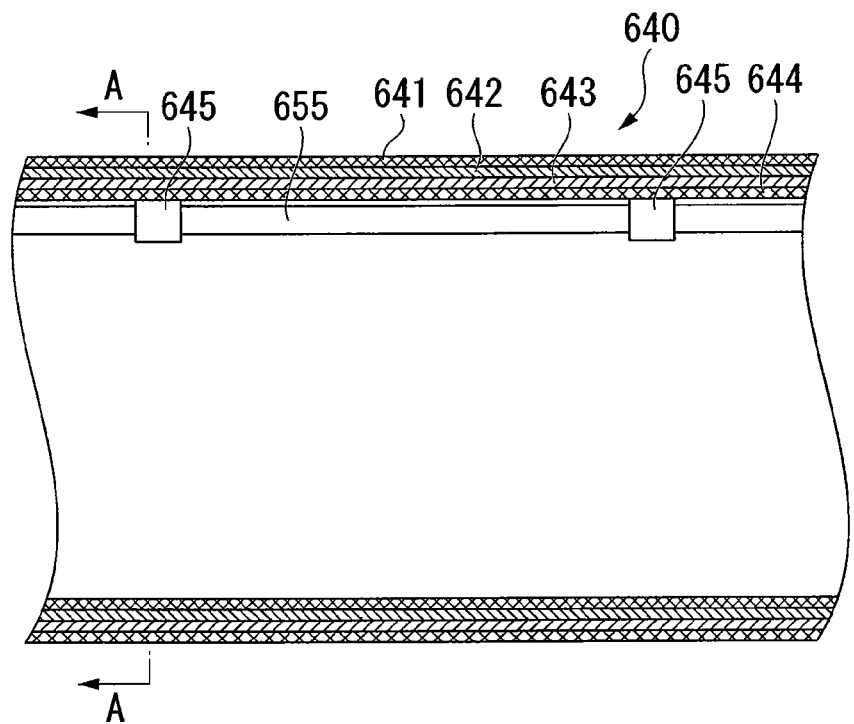
FIGS. 27A and 27B are views showing still another example of a configuration of the inserting portion of the overtube.
Figure 27B:
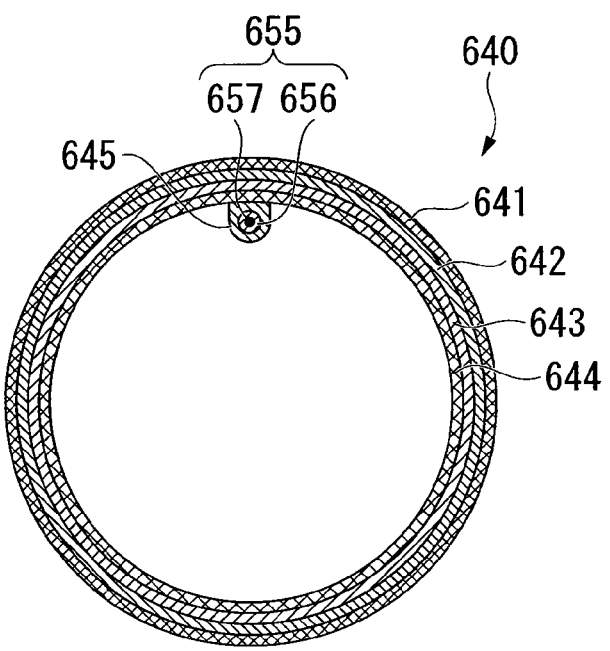

FIGS. 27A and 27B are views showing still another configuration example of the inserting portion 640, FIG. 27A is a cross-sectional view as seen from the side after the inserting portion 640 is cut along the axial direction, and FIG. 27B is a sectional view in the line A-A of FIG. 27A. As shown in FIGS. 27A and 27B, the inner tube layer 644 may be provided with a plurality of insertion pipes 645 in which a through hole which extends in the axial direction of the inserting portion 640, and the transmission portion 655 may be inserted through each of the insertion pipes 645.

Figure 28A:
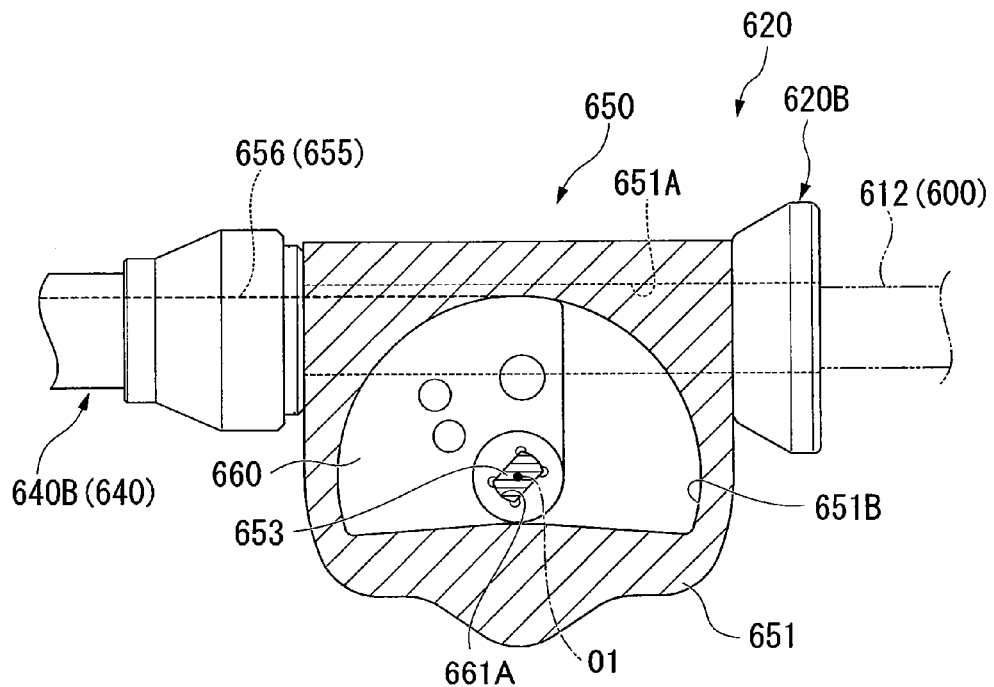
FIGS. 28A and 28B are views showing still another example of a configuration of the inserting portion of the overtube.
Figure 28B:
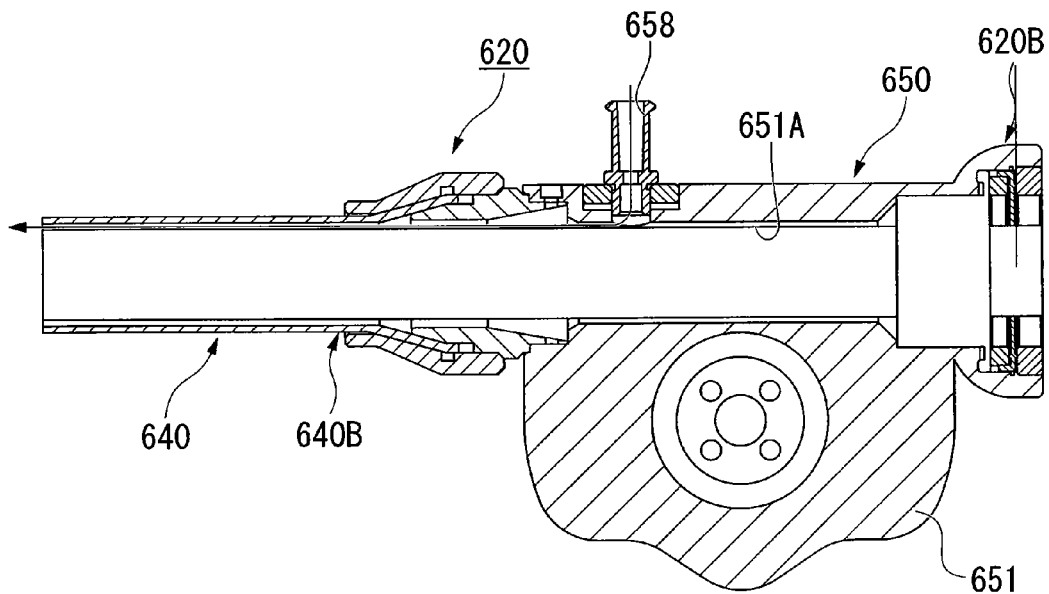

FIGS. 28A and 28B are partial sectional views showing the manipulation portion 650 of the overtube 620 in an enlarged manner.

As shown in FIG. 17, the manipulation portion 650 includes a receiving body 651 fixed to a proximal end 640B of the inserting portion 640, and an manipulation input portion 652 turnably attached to the receiving body 651.

Moreover, as shown in FIGS. 28A and 28B, the manipulation portion 650 includes a pulley (shock-absorbing mechanism) 660 to which the wire 656 of the transmission portion 655 is attached.

The receiving body 651 is formed from, for example, a resin material, a metallic material, and so on, and has a size and weight such that an operator can have in his/her hand. The receiving body 651 is formed with a through hole 651A and a pulley-receiving portion 651B.

The through hole 651A is connected to the proximal end 640B of the inserting portion 640 coaxially with the inserting portion 640. One end of the through hole 651A communicate with the inside of the inserting portion 640, and the other end of the through hole 651B is opened to the outside of the receiving body 651. The size of the internal diameter of the through hole 651A is greater than the external diameter of the inserting portion 612 of the endoscope device 610. In the present embodiment, the cross-sectional shape of the through hole 651A orthogonal to the axial direction is a circular shape.

In addition, the receiving body 651 is formed with a tubular port 658 which has one end opened to the through hole 651A and the other end opened to the outside of the receiving body 651. The port 658 can be used in order to supply a fluid for improving the lubrication of the inserting portion 612 of the endoscope device 610 to the inside of the through hole 651A and the inserting portion 640. In the present embodiment, the port 658 extends in a direction which intersects the through hole 651A.

The pulley-receiving portion 651B supports the pulley 660 inside the receiving body 651 in an oscillating manner. The pulley-receiving portion 651B is arranged at a position opposite to the manipulation input portion 652 with respect to the through hole 651A. The shape of the pulley-receiving portion 651B is a substantially sector form where the turning center O1 of the shaft member 653 becomes a center when the pulley-receiving portion 651B is seen toward a direction in which the shaft member 653 which will be described later extends.

As shown in FIG. 17, the manipulation input portion 652 has a rod-shaped shaft member 653, and a handle portion 654 fixed to the end of the shaft member 653.

As shown in FIG. 28A, the shaft member 653 is turnably supported inside the pulley-receiving portion 651B. In addition, a portion of the outer surface of the shaft member 653 is flatly formed, and the shaft member is fitted to a shaft fitting portion 661A (which will be described later) of the pulley 660. For this reason, when the shaft member 653 is turned around the turning center O1, the pulley 660 turns integrally with the shaft member 653.

The handle portion 654 is formed in the shape of the letter V toward the radial outside from the end of the shaft member 653. The handle portion 654 is formed from, for example, a resin or so on.

Figure 29:
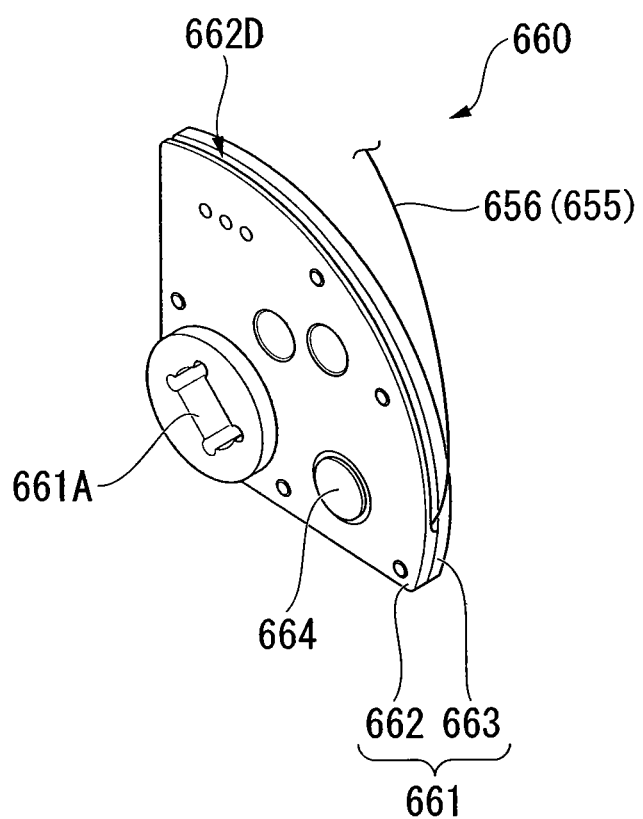
FIG. 29 is a perspective view showing a pulley provided in the manipulation portion.

FIG. 29 is a perspective view showing the pulley 660. As shown in FIG. 29, the pulley 660 is a shock-absorbing mechanism which pulls the wire 656 of the transmission portion 655, and draws a portion of the wire 656 into the inside of the pulley 660 to absorb a change in the relative position between the wire 656 and the pulley 660. The pulley 660 has a substantially sector formed plate-like base 661, and a shaft 664 fitted to the base 661.

Figure 30:
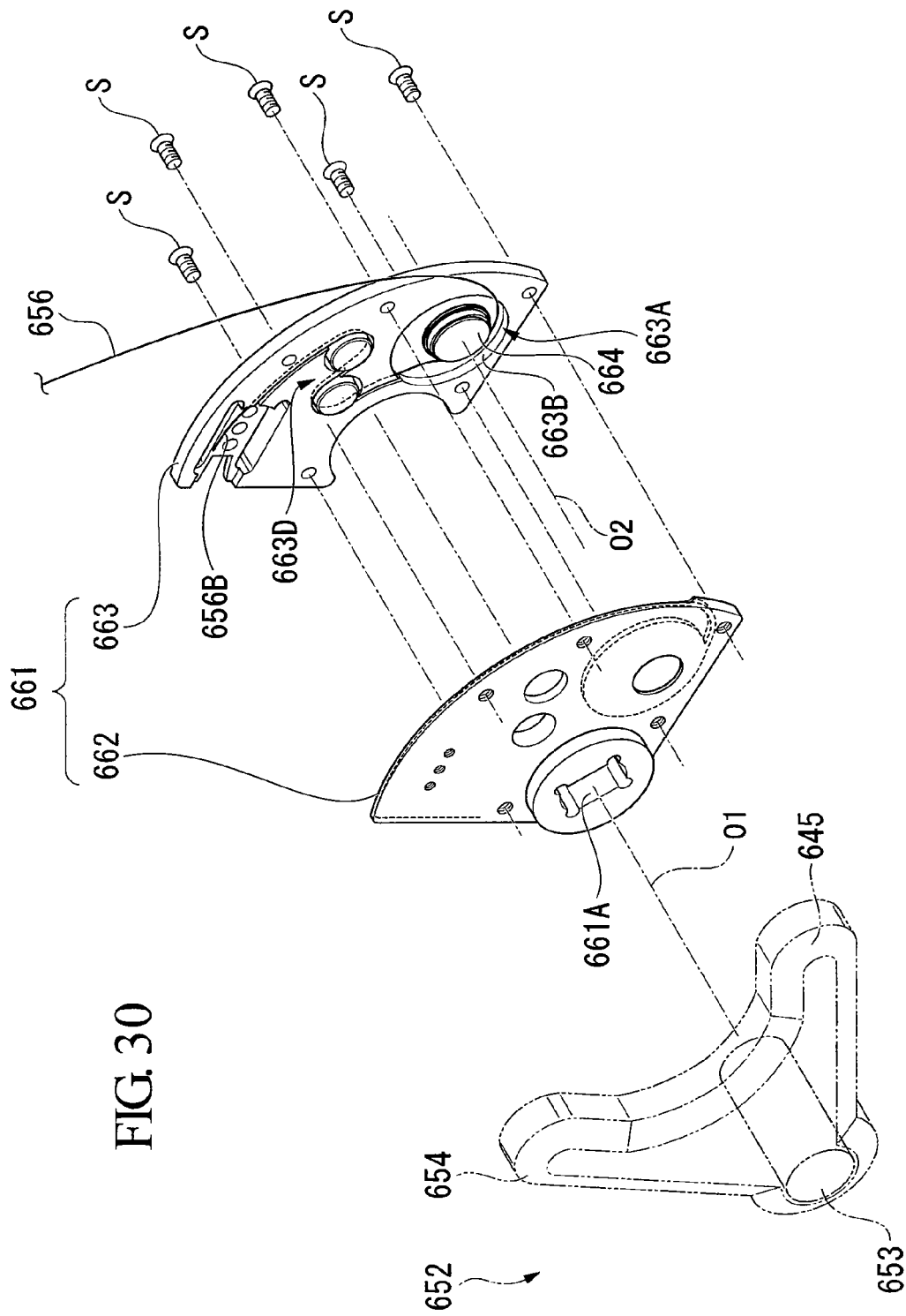
FIG. 30 is an exploded perspective view showing the pulley.
Figure 31:
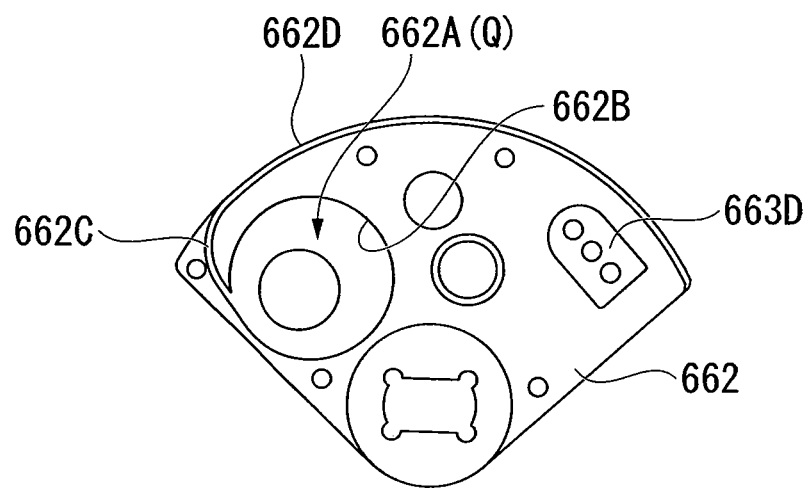
FIG. 31 is a plan view showing a main body of the pulley.
Figure 32:
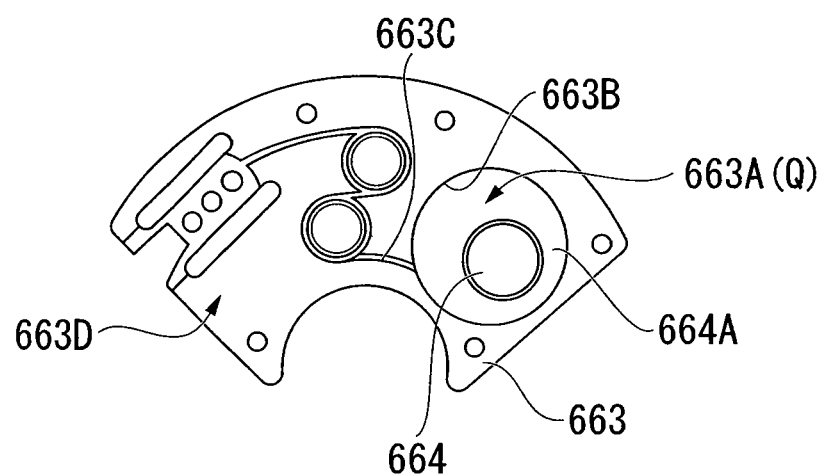
FIG. 32 is a plan view showing a lid of the pulley.

FIG. 30 is an exploded perspective view showing the pulley 660. FIG. 31 is a plan view showing a main body 662 of the pulley 660. FIG. 32 is a plan view showing a lid 663 of the pulley 660. As shown in FIGS. 30 to 32, the shaft fitting portion 661A fitted to the outer surface of the shaft member 653 is formed in the base 661 so as to extend in the thickness direction of the base 661. In addition, the base 661 is provided so that the lid 663 overlaps the substantially sector formed plate-like main body 662. In the present embodiment, the shaft fitting portion 661A has a through hole which passes through the main body 662 in the thickness direction, and is formed in the main body 662.

The main body 662 is formed with a wall portion 662B which defines a shock-absorbing space 662A located at the periphery of the shaft 664, a grooved passage 662C which extends so as to have one end opened to the shock-absorbing space 662A and the other end opened to the outside of the main body 662, and a guide groove 662D which communicates with the passage 662C, and is provided at the outer peripheral surface of the main body 662. In addition, the main body 662 is formed with a through hole which overlaps the shock-absorbing space 662A in the thickness direction of the main body 662 and communicates with the shock-absorbing space 662A in order to attach the shaft 664.

The shock-absorbing space 662A is a substantially columnar shape which is formed so as to be depressed in the thickness direction of the main body 662 from a surface facing the lid 663 when the main body 662 and the lid 663 are combined. In addition, the main body 662 is formed with a circular through hole for positioning and supporting the shaft member 653 so that the through hole passes through the main body 662 in the thickness direction of the main body 662 so as to communicate with the shock-absorbing space 662A.

The wall portion 662B is bent so that the contour shape when the wall portion 662B is seen in the thickness direction of the main body 662 becomes circular.

The passage 662C is formed so as to become a through hole which is opened at one end and the other end as the lid 663 is combined with the main body 662. In the present embodiment, the shape of the passage 662C is bent so as to be directed to the tangential direction of the wall portion 662B at one end and directed to the tangential direction of the guide groove 662D at the other end. The passage 662C preferably has a bent shape such that a bending habit is not formed in the wire 656 located inside the pulley 660, and the wire 656 is not caught by the inner surface of the passage 662C even if the wire 656 is advanced or retreated inside the passage 662C.

The guide groove 662D is depressed toward the center by almost the same length as the diameter of the wire 656 from the outer peripheral side of the sector main body 662, and is provided between the main body 662 and the lid 663. The guide groove 662D is connected to and formed integrally with the passage 662C. In addition, in the present embodiment, although the guide groove 662D is formed in the main body 662, the guide groove 662D may be formed in both the main body 662 and the lid 663.

The lid 663 is formed with a wall portion 663B which defines a shock-absorbing space 663A located at the periphery of the shaft 664, a first groove 663C which is provided to communicate with the shock-absorbing space 663A in a portion of the wall portion 663B in the circumferential direction, and a fixing portion 663D which is provided at the end of the first groove 663C opposite to the side located in the shock-absorbing space 663A. In addition, the lid 663 is formed with a through hole which overlaps the shock-absorbing space 663A in the thickness direction of the lid 663 and communicates with the shock-absorbing space 663A in order to attach the shaft 664.

The shock-absorbing space 663A is provided at a facing position when the main body 662 and the lid 663 are combined together, and the shock-absorbing space 663A is combined with the shock-absorbing space 662A of the main body 662, and become one shock-absorbing space Q. The size of the shock-absorbing space Q measured in the thickness direction of the pulley 660 can be determined according to the number of times which the wire 656 is wound around the shaft 664 in the shock-absorbing space Q.

In the present embodiment, an example in which the number of times which the wire 656 is wound around the shaft 664 in the space surrounded by the wall portions 662B and 663B in the shock-absorbing space Q is 3 times is shown as the shape of the shock-absorbing space Q. At this time, the size of the shock-absorbing space Q measured in the thickness direction of the pulley 660 is a size including three times the diameter of the wire 656 and a clearance whose size is smaller than the diameter of the wire 656.

The wall portion 663B is bent so that the contour shape when the wall portion 663B is seen in the thickness direction of the lid 663 becomes circular.

In the first groove 663C, a portion of the wall portion 663B is cut away and opened to the shock-absorbing space 663A, and the wire 656 is fitted into the first groove 663C. Inside the first groove 663C, the wire 656 may be fixed by, for example, an adhesive or so on.

The fixing portion 663D is provided to fix the wire 656 to the lid 663. The fixing portion 663D has a groove which routes the wire 656 in the shape of the letter S, and is adapted to be able to attenuate the tension applied to the fixing portion of the wire 656. Moreover, the fixing portion 663D sandwiches and fixes the wire 656 between the main body 662 and the lid 663, and screw the main body 662 and the lid 663 in the fixing portion 663D so that the wire 656 can be tighten up.

The shaft 664 is formed in a substantially columnar shape, and is adapted to fit to the main body 662 and the lid 663, respectively. Specifically, the size of the external diameter of both ends of the shaft 664 in the direction of a center axis O2 is made to be smaller than the size of the external diameter of an intermediate portion of a shaft 664 in the direction of the center axis O2. The through holes formed in the main body 662 and the lid 663 in order to attach the shaft 664 are formed in a circular shape such that the size of the internal diameter thereof is almost the same as the size of the external diameter of both ends of the shaft 664. In the present embodiment, the shaft 664 is not fixed to the main body 662 and the lid 663, and the shaft 664 is able to roll around the center axis O2 with respect to the main body 662 and the lid 663. In addition, the shaft 664 may be fixed to the main body 662 or the lid 663. In addition, the shaft 664 may be molded integrally with the main body 662 or the lid 663.

An outer peripheral surface 664A of the shaft 664 is the face around which the wire 656 is wound, and is formed in the shape of a smooth curved surface so as not to damage the wire 656.

Figure 33:
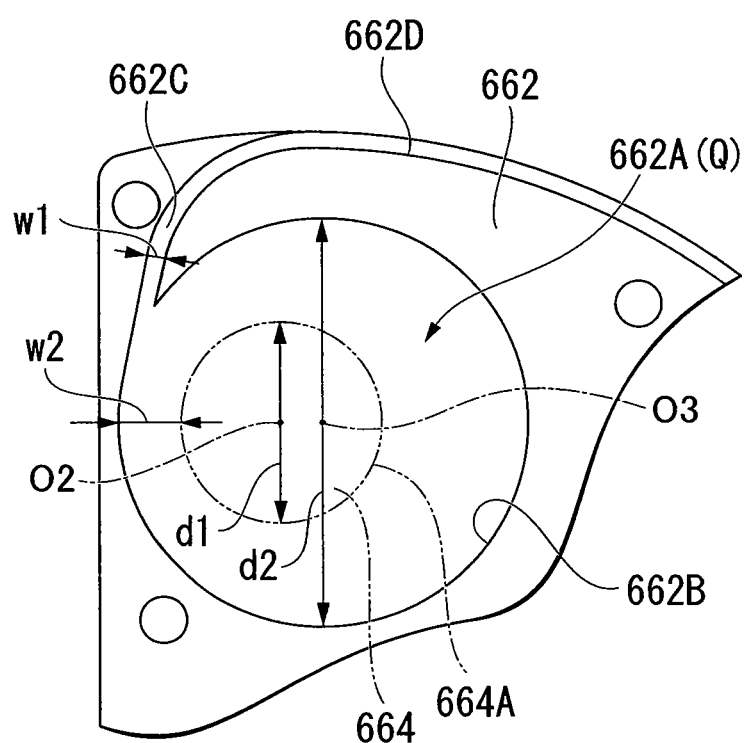
FIG. 33 is an enlarged view showing a portion of the main body of the pulley in an enlarged manner.

FIG. 33 is an enlarged view showing a portion of the main body 662 in an enlarged manner, and shows the portion of the shock-absorbing space Q. As shown in FIG. 33, the shock-absorbing space Q is formed as a cylindrical space by the wall portion 662B (and the wall portion 663B shown in FIG. 30) and the shaft 664. A center axis O3 of the shock-absorbing space Q and the center axis O2 of the shaft 664 are made to be eccentric, and the shortest distance W2 between the wall portion 662B and the outer peripheral surface 664A of the shaft 664 becomes two times to four times the size of the diameter of the wire 656.

In addition, the diameter d2 of the shock-absorbing space Q is greater than the diameter d1 of the shaft 664, and the length of the wire 656 in the shock-absorbing space Q when the wire 656 spreads toward and is wound around the wall portion 662B becomes greater than that when the wire 656 is wound around the outer peripheral surface 664A of the shaft 664.

The operation when the medical system 600 of the present embodiment with the configuration described above is used will be described.

Figure 34:
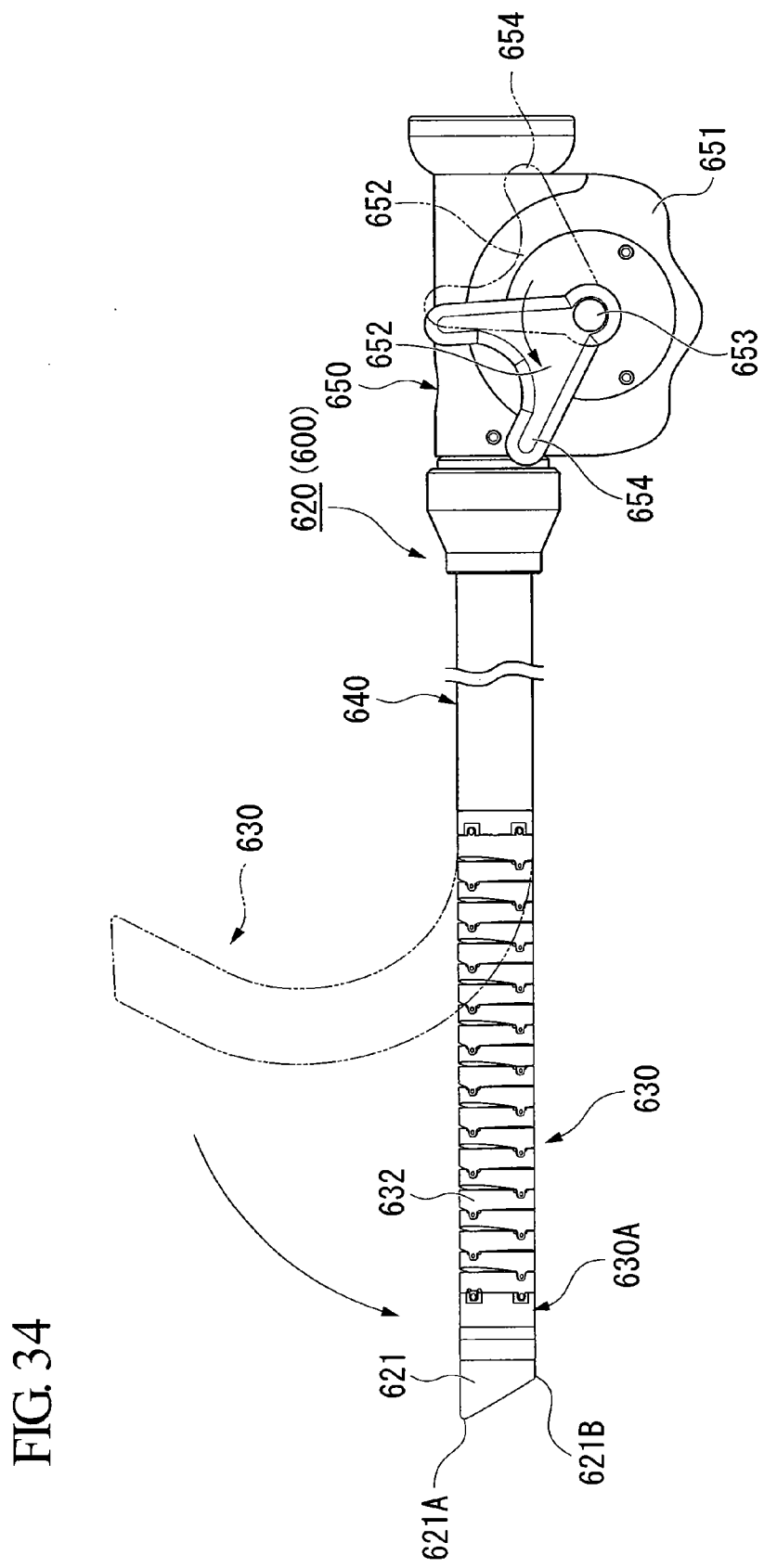
FIG. 34 is an operation explanatory view showing the operation of the overtube when used.

FIG. 34 is an operation explanatory view explaining the operation when the overtube 620 in the medical system 600 of the present embodiment is used. As shown in FIG. 34, when the distal end 640A of the inserting portion 640 is inserted into a body cavity, the handle portion 654 of the manipulation input portion 652 is turned to the distal end of the receiving body 651.

Figure 35A:
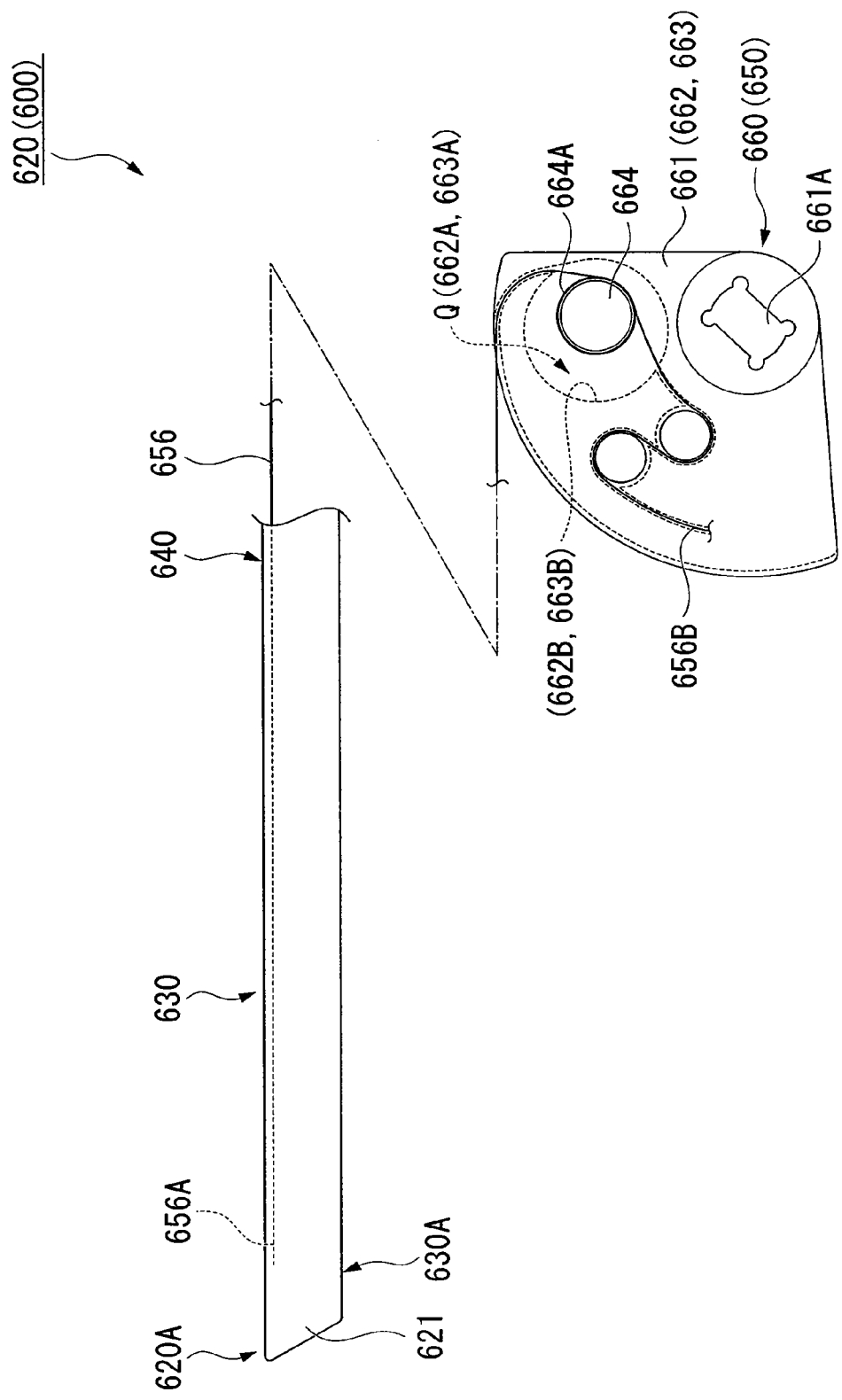
FIGS. 35A and 35B are operation explanatory views showing the operation of the overtube when used.

FIG. 35A is an explanatory view showing the positional relationship of the wire 656 in the pulley 660 when the bending operating portion 630 is in a non-bent state. As shown in FIG. 35A, when the handle portion 654 of the manipulation input portion 652 is turned to the distal end of the receiving body 651, the magnitude of the pulling force of the wire 656 fixed to the distal end 630A of the bending operating portion 630 becomes small, and the bending operating portion 630 is brought into a substantially straight non-bent state due to the elasticity of the bending operating portion 630 itself and the elasticity of the endoscope device. When the bending operating portion 630 is in a non-bent state, the distal end 656A of the wire 656 is pulled toward the distal end 620A of the overtube 620 by the distal end 630A of the bending operating portion 630. At this time, the wire 656 is wound around the outer peripheral surface 664A of the shaft 664 inside the pulley 660.

Figure 35B:
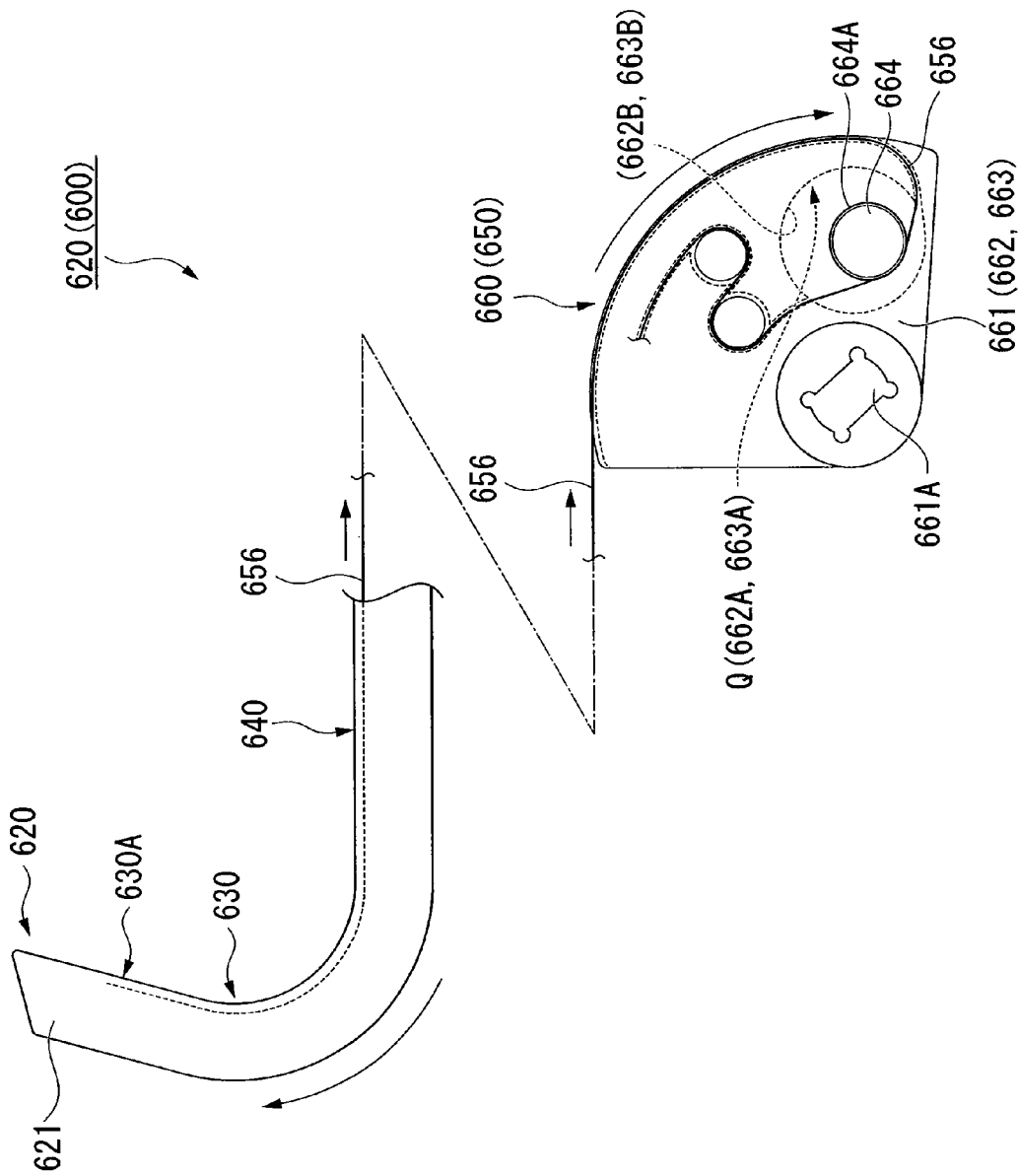

FIG. 35B is an explanatory view showing the positional relationship of the wire 656 in the pulley 660 when the bending operating portion 630 is in a bent state. When the bending operating portion 630 is bent by the manipulation of the manipulation portion 650, the handle 120 is rotationally operated counterclockwise, i.e., toward the proximal end of the overtube 620. Then, as shown in FIG. 35B, the pulley 660 is oscillated and moved toward the proximal end, and the wire 656 is drawn near to the proximal end. When the wire 656 is drawn near to the proximal end, the distal end 630A of the bending operating portion 630 to which the distal end of the wire 656 is connected moves to the proximal end, and thereby the bending operating portion 630 is bent according to the manipulation amount of the handle portion 654.

Figure 36:
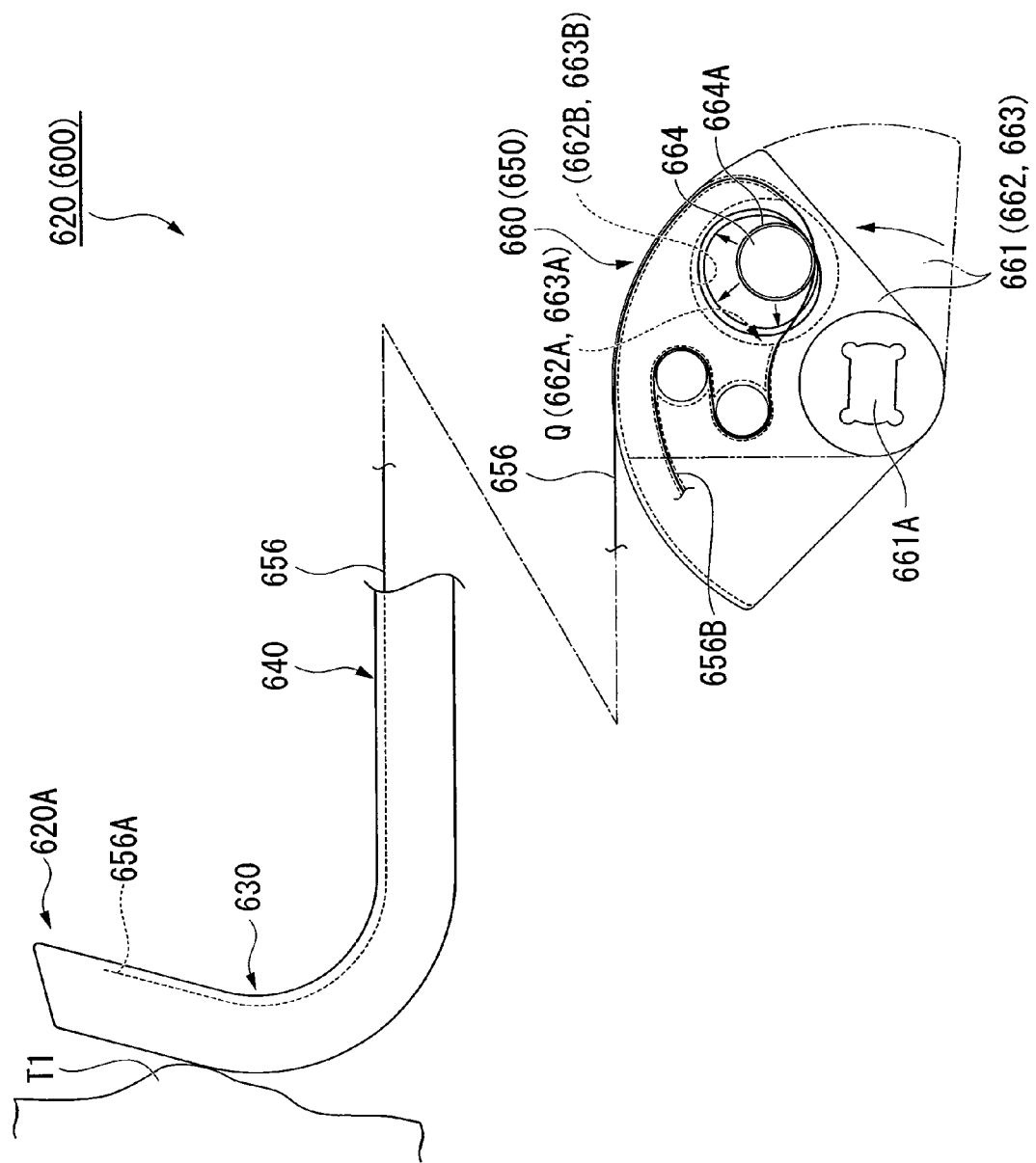
FIG. 36 is an operation explanatory view showing the operation of the overtube when used.

FIG. 36 is an operation explanatory view explaining the operation of the overtube 620 when used. As shown in FIG. 36, in a state in which the overtube 620 is inserted into, for example, a body cavity and the bending operating portion 630 is bent, the portion on the side of the distal end 620A of the overtube 620 may come into contact with a tissue (for example, a tissue T1), and so on in the body cavity.

In this state, when an operator who operates the overtube 620 turns the pulley 660 so as to move the pulley toward the distal end, only the wire 656 is loosened with the bending operating portion 630 remaining in a bent state. In this case, as the pulley 660 oscillates toward the distal end, the wire 656 is pushed into the inside of the pulley 660. Thereby, in the shock-absorbing space Q, the wire 656 wound around the outer peripheral surface 664A of the shaft 664 is loosened, and the ring of the wire 656 spreads toward the wall portions 662B and 663B inside the shock-absorbing space Q. Thereby, the wire 656 which is longer than the length of the wire 656 when being wound three times around the outer peripheral surface 664A of the shaft 664 is stored inside the shock-absorbing space Q. Accordingly, the wire 656 is not loosened or buckled inside the inserting portion 640 and the bending operating portion 630, but is loosened in the shock-absorbing space Q inside the pulley 660.

Figure 37:
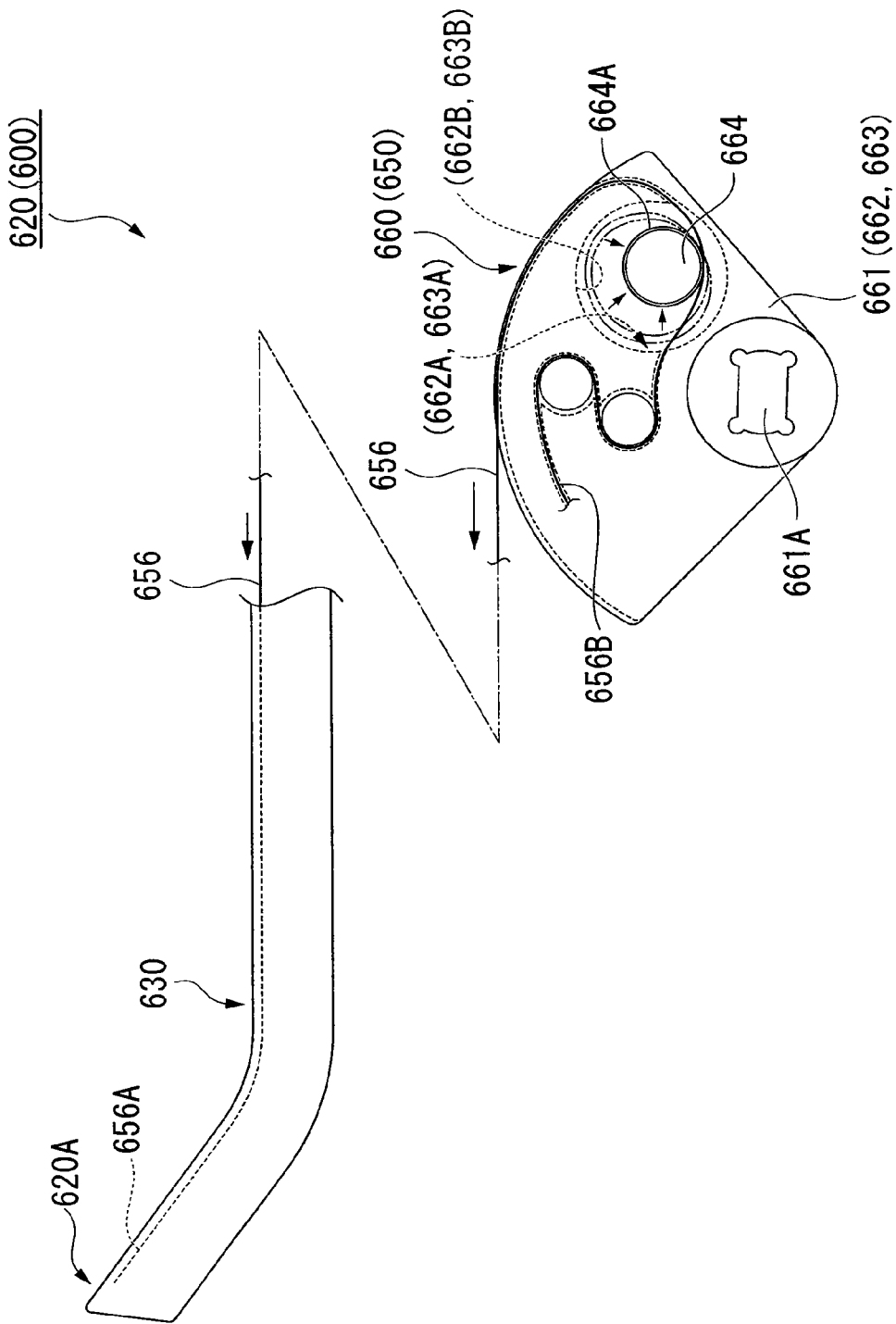
FIG. 37 is an operation explanatory view showing the operation of the overtube when used.

FIG. 37 is an operation explanatory view explaining the operation of the overtube 620 when the distal end 620A of the overtube 620 has been separated from the tissue T1 shown in FIG. 36. As shown in FIG. 37, when the tissue T1 is separated from the distal end 620A of the overtube 620, the bending operating portion 630 deforms so as to be brought in a non-bent state due to the elasticity of the bending operating portion 630 itself and the elasticity of the endoscope device. As the bending operating portion 630 deforms into a non-bent state due to its own elasticity, the wire 656 is pulled out from the pulley 660, and the wire 656 is again wound around the outer peripheral surface 664A of the shaft 664 inside the shock-absorbing space Q.

Figure 38:
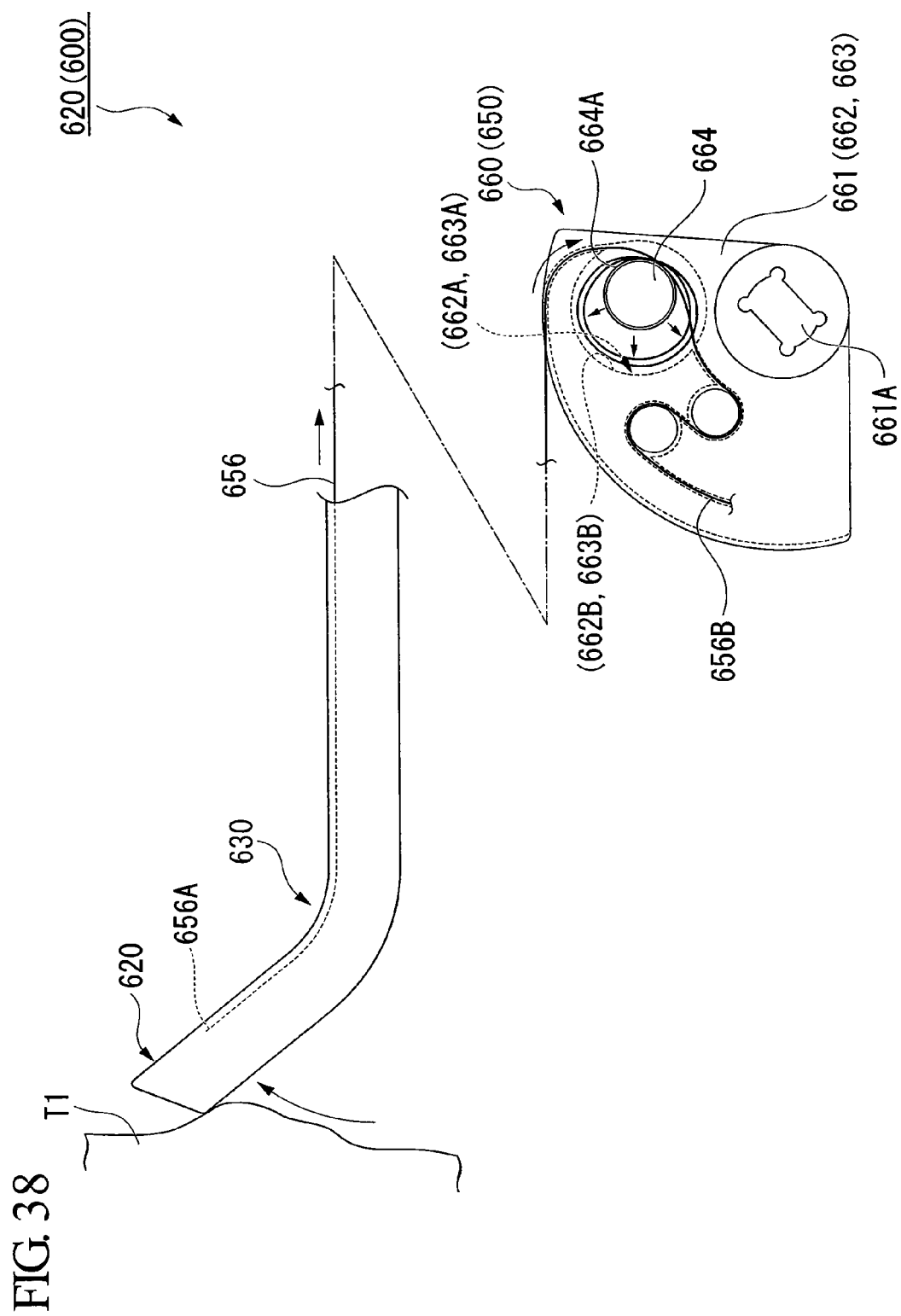
FIG. 38 is an operation explanatory view showing the operation of the overtube when used.

FIG. 38 is an operation explanatory view explaining the operation of the overtube 620 when used. As shown in FIG. 38, in a state in which the overtube 620 has been inserted into, for example, a body cavity, the distal end 620A of the overtube 620 may come into contact with, for example, a tissue (for example, a tissue T1) in the body cavity. In this case, the bending operating portion 630 may be pushed against and bent by the tissue T1 in the body cavity. At this time, despite the manipulation portion 650 of the overtube 620 is in a positional relationship of bringing the bending operating portion 630 into a non-bent state, the bending operating portion 630 is bent due to an external force.

In addition, even when the overtube 620 is not used, if the overtube 620 is transported, or the preparation for using the overtube 620 is performed, similarly to the above, the bending operating portion 630 may be bent due to an external force.

In this case, as the bending operating portion 630 is bent, the wire 656 is pressed toward the manipulation portion 650. The wire 656 is pushed into the inside of the pulley 660 on the side of the manipulation portion 650. Thereby, in the shock-absorbing space Q, the wire 656 wound around the outer peripheral surface 664A of the shaft 664 is loosened, and the ring of the wire 656 spreads toward the wall portions 662B and 663B inside the shock-absorbing space Q. Thereby, the wire 656 which is longer than the length of the wire 656 when being wound three times around the outer peripheral surface 664A of the shaft 664 is stored inside the shock-absorbing space Q. Accordingly, the wire 656 is not loosened or buckled inside the inserting portion 640 and the bending operating portion 630, but is loosened in the shock-absorbing space Q inside the pulley 660.

Conventionally, in a medical instrument in which a bending operating portion provided in an inserting portion is bent using a wire, when the wire has been loosened inside the bending operating portion or the inserting portion, there is a possibility that the wire may be buckled or twisted inside the bending operating portion or the inserting portion, and as a result the wire may be broken.

On the other hand, according to the overtube 620 of the present embodiment, a portion of the wire 656 is stored inside the shock-absorbing space Q by the pulley (shock-absorbing mechanism) 660 provided in the manipulation portion 650. Thereby, when the wire 656 has been loosened inside the bending operating portion 630 and the inserting portion 640, the wire 656 is drawn into the shock-absorbing space Q, and the wire 656 is hardly loosened or buckled inside the bending operating portion 630 and the inserting portion 640. As a result, it is possible to reduce the possibility that the wire 656 may be bent or twisted, and as a result, the wire may be broken, and thereby the bending operating portion 630 can be smoothly bent.

In addition, in the present embodiment, the wire 656 is wound around the shaft 664 three times. As the wire 656 is wound around a plurality of times, the length of the wire 656 which can be drawn into the shock-absorbing space Q can be increased without significantly increasing the size of the shock-absorbing space Q compared to the case where the wire 656 is wound around the shaft 664 only once.

Moreover, since the main body 662 and lid 663 of the base 661 are formed with the wall portions 662B and 663B which define a portion of the extension of the shock-absorbing space Q, when a wire 656 has spread inside the shock-absorbing space Q, the wire 656 can be supported by the wall portions 662B and 663B, and the outer surface of the wire 656 can be pushed back by the wall portions 662B and 663B. Thereby, the length of the wire 656 which is drawn into the shock-absorbing space Q can be determined by the wall portions 662B and 663B.

In addition, since the base 661 oscillates around the shaft member 653 which is a straight line parallel to the center axis O2 of the shaft 664 and pulls the proximal end 656B of the wire 656, the bending of the bending operating portion 630 can be operated by turning the handle portion 654 fixed to the shaft member 653.

In addition, since the insertion pipe 636 is formed in each of the bending pieces 632 provided in the bending operating portion 630, the possibility that the wire 656 is loosened and buckled such that the wire 656 jumps out to the inside of the bending operating portion 630 can be reduced.

In addition, since the flexible layer 643 provided in the inserting portion 640 is formed from a long member spirally wound around the center axis of the inserting portion 640, the inserting portion 640 can be made flexible.

In addition, since the inserting portion 640 has the blade tube layer 642 on the outside of the flexible layer 643 and the transmission portion 655 is arranged between the flexible layer 643 and the blade tube layer 642, the possibility that the wire 656 meanders inside the inserting portion 640 can be reduced.

In addition, conventionally, the transmission portion for bending these tubes, for example, of the inserting portion may not be fixed to these tubes. In this case, when an endoscope device, for example, is used while being inserted the inserting portion, there is a possibility that the endoscope device and the transmission portion may interfere with each other, and the resistance when the endoscope device is inserted into the inserting portion of the overtube, or the endoscope device is operated to advance or retreat within the inserting portion of the overtube may increase.

On the other hand, according to the overtube 620 of the present embodiment, since the transmission portion 655 is configured so that the coiled tube 657 is fixed between the flexible layer 643 and the blade tube layer 642 of the inserting portion 640, and the wire 656 is inserted into an inner cavity of the coiled tube 657 so as to be able to advance or retreat, when the endoscope device is inserted into the inserting portion 640 of the overtube 620, the interference between an endoscope device and the transmission portion 655 can be mitigated.

Modified Example

The configuration of a modified example of the above-described overtube 620 will be described with reference to FIGS. 39 to 41B.

Figure 39:
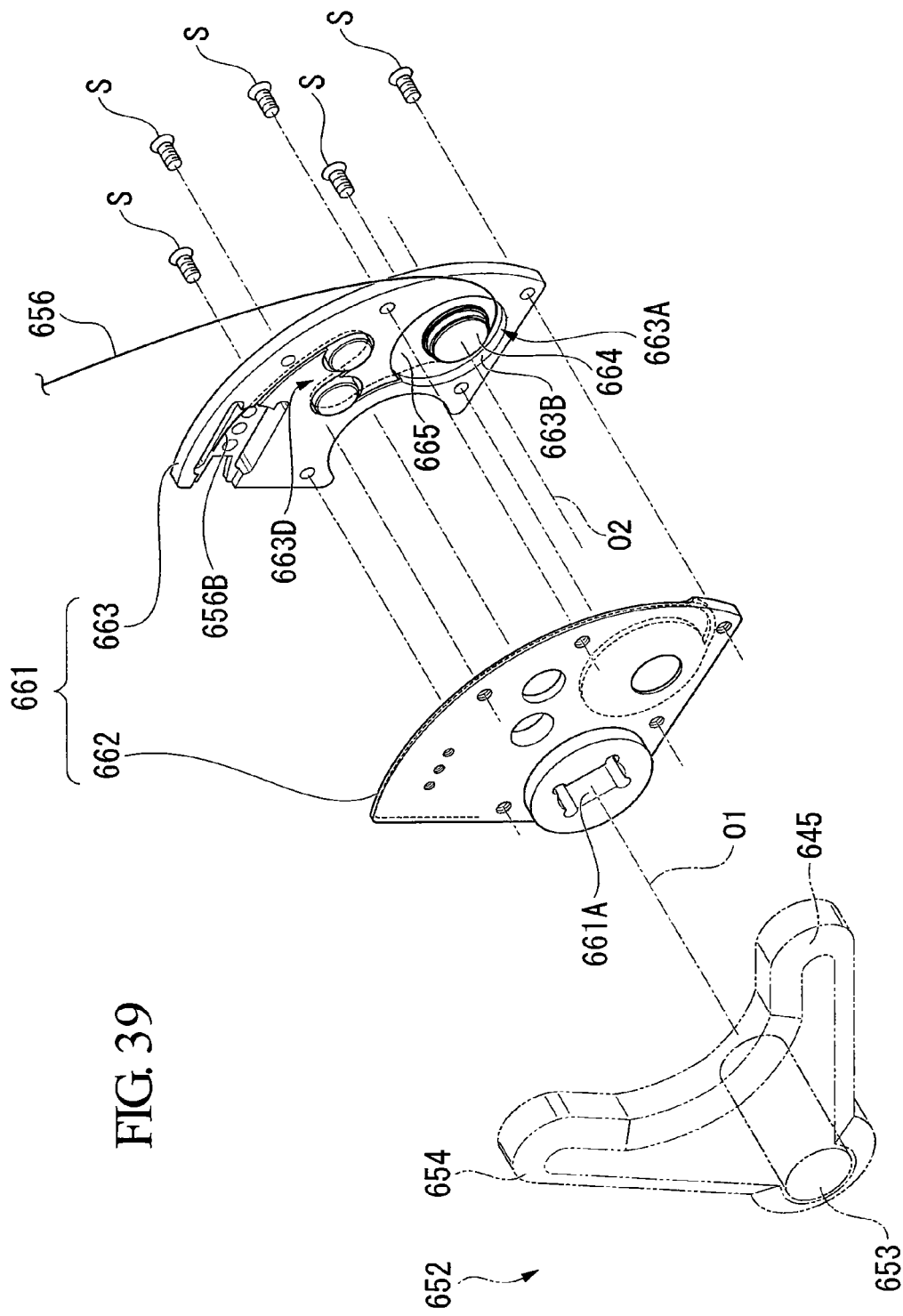
FIG. 39 is an exploded perspective view showing the configuration of a pulley in a modified example of the overtube.
Figure 40A:
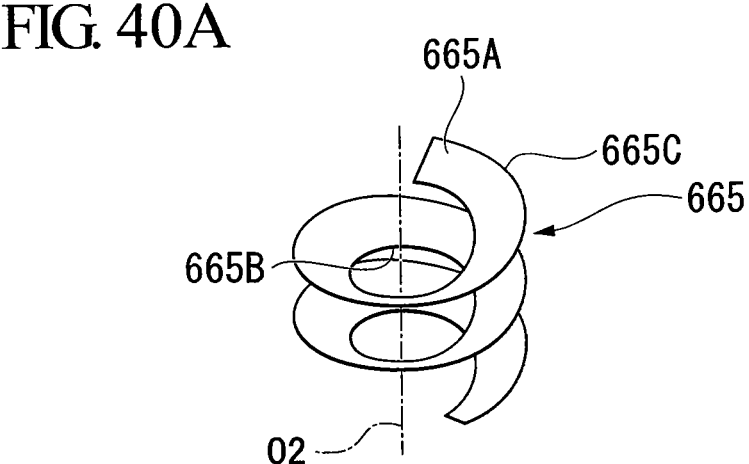
FIG. 40A is a perspective view showing a partition wall member provided in the pulley of the modified example.
Figure 40B:
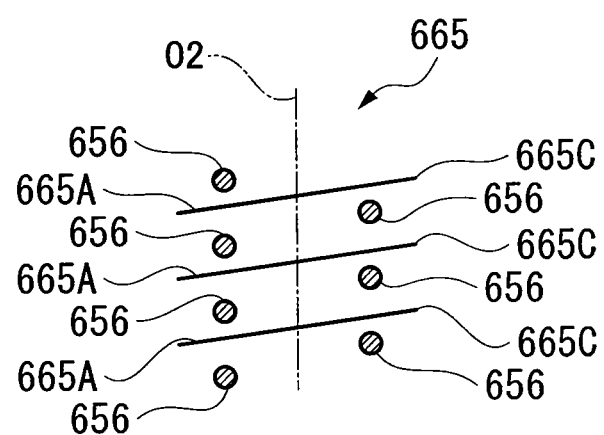
FIG. 40B is a schematic view schematically showing a state in which a wire has been combined with the partition wall member.

FIG. 39 is an exploded perspective view showing the configuration of a pulley in a modified example of the overtube. In addition, FIG. 40A is a perspective view showing a partition wall member provided in the pulley of the modified example, and FIG. 40B is a schematic view schematically showing a state in which a wire has been combined with the partition wall member.

As shown in FIG. 39, in the present modified example, a partition wall member 665 is arranged in the shock-absorbing space 663A of the pulley 660. As shown in FIGS. 39 to 40B, the partition wall member 665 is provided to align the wire 656 so that the wire is not entangled inside the shock-absorbing space Q (the shock-absorbing space 662A and the shock-absorbing space 663A shown in FIG. 31 and FIG. 32). The partition wall member 665 is formed with a spiral wall portion 665A which spirally extends around the center axis O2 of the shaft 664 as it goes toward the thickness direction of the pulley 660 when the partition wall member 665 has been arranged in the shock-absorbing space Q, an inner peripheral portion 665B which fits to the outer peripheral surface 664A of the shaft 664 on the radial inside of the spiral wall portion 665A, and an outer peripheral portion 665C which abuts on each of the wall portions 662B and 663B which define the shock-absorbing space Q. The material of the partition wall member 665 is preferably a material with a small coefficient of friction with the outer surface of the wire 656. In addition, the partition wall member 665 is preferably formed from a hard material such that a spiral shape can be maintained inside the shock-absorbing space Q. Specifically, as the material of the partition wall member 665, fluororesin, other resin materials, and nonwoven fabric, paper, and so on which has been subjected to surface treatment which reduces the frictional resistance with the wire 656 can be employed.

In the present modified example, the dimension of the shock-absorbing space Q measured in the thickness direction of the pulley 660 is a size including three times the diameter of the wire 656, the thickness of the partition wall member 665 which will be described later, and a clearance whose size is smaller than the diameter of the wire 656.

Next, the operation of the overtube 620 of the modified example when used will be described mainly about the action of the partition wall member 665. FIG. 41A is an operation explanatory view explaining the operation of the overtube of the modified example when used, and FIG. 41B is an explanatory view explaining the function of the partition wall member.

As shown in FIG. 41A, the wire 656 which is loosened in the shock-absorbing space Q of the pulley 660 is wound around the shaft 664, for example, when the bending operating portion 630 is brought into a non-bent state from a bent state. As shown in FIG. 41B, the partition wall member 665 supports the wire 656 wound around the shaft 664 in the shock-absorbing space Q with each one distinguished. For this reason, the wire 656 is guided to the outer peripheral surface 664A of the shaft 664 along the spiral wall portion 665A of the partition wall member 665.

In the present modified example, since the partition wall member 665 is provided inside the shock-absorbing space Q, the wire 656 does not intersect each other inside the shock-absorbing space Q, and the wire 656 is not entangled inside the shock-absorbing space Q. Moreover, since the wire 656 is guided to the outer peripheral surface 664A of the shaft 664 along the spiral wall portion 665A of the partition wall member 665, the wire 656 can be wound around the outer peripheral surface 664A of the shaft 664, without entanglement of the wire 656.

In addition, even when the number of windings of the wire 656 wound inside the shock-absorbing space Q is further increased, the partition wall member 665 can keep the wire 656 from being entangled.

Although the preferable embodiments of the present invention have been described hitherto, the present invention is not limited to these embodiments. Additions, omissions, substitutions, and other modifications can be made without departing from the spirit or scope of the present invention.

For example, in the above-described respective embodiments, the plane P1 on which the manipulation stick 82 oscillates and the plane P2 on which the second oscillating portion oscillates are made to be orthogonal to each other. However, the plane P1 and the plane P2 may be made to intersect each other.

In addition, in the above-described third embodiment, for example, a so-called high-tension wire of which the strength has been increased by heat treatment, for example, can be used as the wire 656 for manipulating the bending operating portion 630. In this case, a configuration can be provided in which breaking of the wire is hardly caused during manipulation while the internal diameter of the inserting portion 640 is largely maintained by making the diameter of the wire 656 small.

In addition, coating (not shown) composed of polytetrafluoroethylene (PTFE) can also be performed on the surface of the wire 656. In this case, the friction between the coiled tube 657 or the insertion pipe 636, and the wire 656 can be reduced, and the force applied to the wire 656 can be efficiently transmitted to the bending operating portion 630.

Moreover, the frictional resistance between the wire 656 and the partition wall member 665 can be further reduced.

As the friction between the coiled tube 657, the insertion pipe 636, or the partition wall member 665, and the wire 656 is reduced, the force made to be generated in the wire 656 can be made small. Thus, the bending operating portion 630 can be bent using a smaller diameter wire. Instead of PTFE, Defric coat, silicon oil, and so on may be used for the wire 656 in order to reduce the friction with the coiled tube 657 or the insertion pipe 636.

In addition, when a high-tension wire is adopted as the wire 656, the wire 656 becomes straight in a natural state due to the elasticity of wire 656 itself, and the wire 656 has a force which deforms in a direction away from the outer peripheral surface 664A of the shaft 664 due to the elasticity of the wire 656 itself inside the shock-absorbing space Q of the pulley 660. Accordingly, when the tension to pull out the wire 656 to the outside of the pulley 660 from the passage 662C is not applied to the wire 656, the wire 656 can draw the wire 656 into the pulley 660 due to the elasticity of the wire 656 itself.

When the wire 656 is formed from a material having elasticity in this way, the a wire 656 can be drawn into the pulley 660 due to the elasticity of the wire 656 itself, the wire 656 is more easily drawn into the shock-absorbing space Q inside the pulley 660, and loosening of the wire 656 in the bending operating portion 630, the inserting portion 640, and so on of the overtube 620 can be further reduced.

In addition, even if the wire 656 is not a high-tension wire of which the strength has been raised by heat treatment, and so on, for example, even if the wire 656 is formed from general stainless steel, the wire 656 can be similarly drawn into the pulley 660 due to the elasticity of the wire 656 itself. When a metal wire rod is adopted as the material of the wire 656, for example, iron-based alloy materials, such as steel, pig iron, titanium, and stainless steel; aluminum-based alloy materials; and so on can be adopted.

In addition, the overtube 620 and pulley (shock-absorbing mechanism) 660 which have been described in the third embodiment exert the following effects besides a state in which the distal end 620A of the overtube 620 is pressed against the tissue T1, for example, even in a situation which time lag occurs until the manipulation input to the manipulation input portion 652 is too fast and the bending operating portion 630 operates actually. That is, if the speed at which the handle portion 654 is turned is fast when returning to a non-bent state from the state where the bending operating portion 630 is bent, the wire 656 may be loosened before the bending operating portion 630 returns to a non-bent state due to the elasticity of the bending operating portion 630 itself. When the wire 656 is loosened, the wire 656 is supported by the friction between the outer surface of the wire 656 and the bending operating portion 630 or the inserting portion 640, and the wire 656 sags within the receiving body 651 of the manipulation portion 650.

Inside the receiving body 651, the wire 656 is pushed in toward the shock-absorbing space Q inside the pulley 660 as the pulley 660 turns to the distal end. In the shock-absorbing space Q, the wire 656 wound around the outer peripheral surface 664A of the shaft 664 is loosened, and the ring of the wire 656 spreads toward the wall portions 662B and 663B inside the shock-absorbing space Q. Thereby, the wire 656 which is longer than the length of the wire 656 when being wound three times around the outer peripheral surface 664A of the shaft 664 is stored inside the shock-absorbing space Q. Accordingly, the wire 656 is not loosened or buckled inside the inserting portion 640 and the bending operating portion 630, but is loosened in the shock-absorbing space Q inside the pulley 660.

When the wire 656 is loosened in the shock-absorbing space Q inside the pulley 660, the wire 656 is located in a space between each spiral wall portion 665A of the partition wall member 665, and does not intersect each other. For this reason, the wire 656 is not entangled inside the shock-absorbing space Q.

As the bending operating portion 630 deforms into a non-bent state due to its own elasticity, the wire 656 is pulled out from the pulley 660, and the wire 656 is again wound around the outer peripheral surface 664A of the shaft 664 inside the shock-absorbing space Q. At this time, since the wire 656 is guided to the outer peripheral surface 664A of the shaft 664 along the spiral wall portion 665A of the partition wall member 665, the wire 656 can be aligned and wound around the outer peripheral surface 664A of the shaft 664, without entanglement of the wire 656.

In addition, the present invention is not limited by the above description and is limited only by the scope of the appended claims.

The invention claimed is:

1. A medical instrument comprising:
   a tubular inserting portion extending along a longitudinal axis and having a tubular bending operation portion which is bendable; and
   a wire member disposed in the inserting portion along the longitudinal axis and which bends the bending operation portion in a predetermined direction by being moved toward the inserting portion;
   a manipulation portion to which a first end of the wire member is fixed and which moves the wire member by being operated;
   wherein the manipulation portion includes:
      a shaft portion around which a portion of the wire member is wound,
      a pair of faces provided to be separated in an axial direction of the shaft portion, and
      a wall portion which connects the pair of faces,
   a shock absorbing space, which communicates with an inside of the inserting portion, is defined by the pair of faces, the wall portion, and an outer peripheral surface of the shaft portion,
   a second end of the wire member is fixed to the bending operation portion, and
   when the bending operation portion is bent in the predetermined direction by an external force applied to the bending operation portion, a portion of the wire member is moved into the shock-absorbing space and makes a ring whose diameter is larger than a diameter of the shaft portion.

2. The medical instrument according to claim 1, wherein the bending operating portion has a plurality of bending pieces which are formed in a tubular shape and connected to each other, and each of the plurality of bending pieces has an insertion pipe through which the wire member is inserted.

3. The medical instrument according to claim 1, wherein the inserting portion has an outer sheath, and an inner sheath arranged inside the outer sheath, and the wire member is arranged between the outer sheath and the inner sheath.

4. The medical instrument according to claim 3, wherein an intermediate sheath made of a long member spirally wound around a center axis of the inserting portion is provided between the outer sheath and the inner sheath, and the wire member is arranged between the intermediate sheath and the inner sheath.

5. The medical instrument according to claim 1, wherein the manipulation portion is configured to be rotatable around a predetermined rotational axis,
   the shaft portion is provided so as to be eccentric to the rotational axis, and
   when the manipulation portion is rotated around the rotational axis, the shaft portion moves around the rotational axis.

6. The medical instrument according to claim 5, wherein when the shaft portion moves around the rotational axis under a condition where the bending operation portion is bent in the predetermined direction by the external force, the wire member makes the ring.

* * * * *